(12) United States Patent
Alwatban et al.

(10) Patent No.: US 12,076,128 B2
(45) Date of Patent: Sep. 3, 2024

(54) METHODS OF EVALUATING CEREBROVASCULAR REACTIVITY USING TRANSCRANIAL DOPPLER

(71) Applicant: NUtech Ventures, Lincoln, NE (US)

(72) Inventors: Mohammed Alwatban, Riyadh (SA); Gregory R. Bashford, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 778 days.

(21) Appl. No.: 16/819,140

(22) Filed: Mar. 15, 2020

(65) Prior Publication Data

US 2020/0288994 A1 Sep. 17, 2020

Related U.S. Application Data

(60) Provisional application No. 62/819,200, filed on Mar. 15, 2019.

(51) Int. Cl.
| | |
|---|---|
| *A61B 5/0285* | (2006.01) |
| *A61B 5/00* | (2006.01) |
| *A61B 5/0205* | (2006.01) |
| *A61B 5/021* | (2006.01) |
| *A61B 5/08* | (2006.01) |
| *A61B 5/087* | (2006.01) |
| *C07K 16/28* | (2006.01) |
| *A61K 38/00* | (2006.01) |

(52) U.S. Cl.
CPC .......... *A61B 5/0285* (2013.01); *A61B 5/0205* (2013.01); *A61B 5/02133* (2013.01); *A61B 5/082* (2013.01); *A61B 5/087* (2013.01); *A61B 5/4088* (2013.01); *A61B 5/4836* (2013.01); *C07K 16/28* (2013.01); *A61K 38/00* (2013.01)

(58) Field of Classification Search
CPC ........................... A61B 5/0285; A61B 5/0205
USPC ....................................................... 600/485
See application file for complete search history.

(56) References Cited

U.S. PATENT DOCUMENTS

| | | | |
|---|---|---|---|
| 2006/0079773 A1* | 4/2006 | Mourad | A61B 5/031 600/438 |
| 2010/0301860 A1* | 12/2010 | Kim | G01R 33/50 324/309 |
| 2016/0278736 A1* | 9/2016 | Hamilton | A61B 8/06 |

* cited by examiner

*Primary Examiner* — Nicole F Lavert
(74) *Attorney, Agent, or Firm* — Womble Bond Dickinson (US) LLP

(57) ABSTRACT

Provided here are methods of detecting compromised cerebrovascular reactivity in a subject and treating such subject. The method includes acquiring transcranial Doppler signals and cardiac measurements from the subject following a breath-hold maneuver and recording a test set of CBFV measurements. A breath-hold acceleration index is calculated based on a linear regression correlation of temporal variations of the mean velocity across all cardiac cycles during the breath-hold maneuver. The presence of compromised cerebrovascular reactivity in the subject is detected in response to variations in the breath-hold acceleration index of the subject as compared to a healthy individual performing breath-hold maneuver under similar conditions. If the subject has compromised cerebrovascular reactivity, a therapeutically effective compound is administered to the subject along with provision of behavioral modification regimen.

20 Claims, 9 Drawing Sheets

METHODS OF EVALUATING CEREBROVASCULAR REACTIVITY USING TRANSCRANIAL DOPPLER

CROSS-REFERENCE TO RELATED APPLICATION

This application claims the benefit of and priority to U.S. Provisional Application No. 62/819,200, filed Mar. 15, 2019.

TECHNICAL FIELD

The disclosure relates to methods of evaluating cerebrovascular reactivity using a transcranial Doppler system. The disclosure also relates to methods of determining compromised cerebrovascular reactivity using a transcranial Doppler system and treatments thereof.

BACKGROUND

Alzheimer's disease is a cognitive disease and the most common cause of dementia. A substantial overlap exists among abnormality in cerebral vasoreactivity (CVR) and symptomatic Alzheimer's disease. CVR reflects the ability of cerebral vessels to dilate in response to an increase in $CO_2$. CVR can be quantified using transcranial Doppler (TCD) measurement of cerebral blood flow velocities (CBFV) in the middle cerebral artery with $CO_2$ as a vasodilatory stimulus. TCD ultrasound is a noninvasive and cost-effective sensing modality that measures CBFV with high temporal resolution. Cerebrovascular damage is present in early stages of chronic diseases such as heart disease, stroke, type 2 diabetes, obesity, hypertension and Alzheimer's (AD). CBFV increases in response to an increase in arterial $CO_2$ (hypercapnia). This increase in CBFV is produced by a change in the diameter of cerebral arterioles and capillaries, which is measured as CVR. CVR is used to detect cerebrovascular damage. CVR should not be confused with cerebral autoregulation (CA), a process which maintains CBFV in normal range when cerebral perfusion pressure changes. Inspired $CO_2$ and performing a breath-hold maneuver are two of the most common approaches for the induction of hypercapnia when measuring CVR with TCD. Initially, inspiring $CO_2$ was the conventional method to measure CVR. However, the method suffered from various problems such as awkwardness of external equipment, dyspnea, and elevated anxiety especially in elderly subjects. These problems were alleviated in part with the breath-hold maneuver, which offered a simplified method for inducing hypercapnia as an alternative to inspiring $CO_2$. The breath-hold maneuver is a very convenient method to estimate CVR as it needs no external stimulus to build partial pressures of $CO_2$ ($PaCO_2$). This method only requires a flow measurement device to measure CBFV and subject cooperation to perform the breath-hold maneuver. The simplicity of the method makes the breath-hold maneuver ideal for screening large populations in normal hospital settings.

The current parameter used to estimate CVR using the breath-hold maneuver is known as the breath-holding index (BHI). This index, commonly used for nearly 25 years, is defined as the maximum percentage increase in CBFV divided by the breath-holding time. For example, in the past 8 years, many small cross-sectional TCD studies have found CVR to be lower in patients with Alzheimer's disease compared with healthy controls, and some longitudinal studies have shown CVR to be lower in patients several years before showing symptoms of dementia using the BHI. Also, some longitudinal studies have shown the ability of BHI to identify subjects with asymptomatic carotid stenosis eventually leading to dementia. Both groups of studies show the promise of BHI as a predictive tool for cognitive decline. However, though simple to calculate, BHI suffers from low reproducibility and high variability. Also, previous studies have shown conflicting correlative relationships between BHI and inspired $CO_2$. Correlations range from weak ($r=0.38$; $P<0.01$) to strong ($r=0.77$, $P<0.01$). It has been shown that inaccurate breath-hold execution is a major contributing factor to such conflicting results. Moreover, there have been conflicting results on whether CVR is affected by body position, even in healthy subjects.

SUMMARY

Disclosed herein are methods to address the shortcomings of the art, and may provide any number of additional or alternative advantages, including more effective methods for evaluating cerebrovascular reactivity and detecting compromised cerebrovascular reactivity. Disclosed here are methods of detecting preclinical Alzheimer's disease by determining the breath-hold acceleration index (BHAI) for a subject subsequent to a breath-holding maneuver.

Disclosed is a method of detecting compromised cerebrovascular reactivity in a subject. The method includes the steps of acquiring a set of transcranial Doppler signals from a subject during performance of a breath-hold maneuver by the subject and calculating cerebral blood flow velocity (CBFV) measurements in response to the set of transcranial Doppler signals; acquiring a set of cardiac measurements of the subject during performance of the breath-hold maneuver, wherein the set of cardiac measurements include systolic velocity (Vs) and diastolic velocity (Vd) in each cardiac cycle for cardiac cycles during the breath-hold maneuver; calculating, using a processor, a mean velocity by averaging the CBFV measurements within each cardiac cycle; calculating, using the processor, a breath-hold acceleration index based on a linear regression correlation of temporal variations of the mean velocity across all cardiac cycles during the breath-hold maneuver; and detecting presence of compromised cerebrovascular reactivity in the subject in response to a breath-hold acceleration index of the subject being more than one standard deviation less than a breath-hold acceleration index of a healthy individual performing breath-hold maneuver under similar conditions as the subject. In an embodiment, the compromised cerebrovascular reactivity is indicative of preclinical Alzheimer's disease. In an embodiment, the compromised cerebrovascular reactivity is indicative of Alzheimer's disease in response to the breath-hold acceleration index of the subject being more than two standard deviations less than a breath-hold acceleration index of a healthy individual performing breath-hold maneuver under similar conditions as the subject. In an embodiment, the method further comprises the step of calculating, using the processor, a pulsatility index for each cardiac cycle during the breath-hold maneuver, wherein the pulsatility index is the quotient when the difference in the systolic velocity (Vs) and diastolic velocity (Vd) in each cardiac cycle is divided by the mean velocity; detecting presence of compromised cerebrovascular reactivity in the subject in response to an increased pulsatility index and a breath-hold acceleration index of the subject being more than one standard deviation less than a breath-hold acceleration index of a healthy individual performing breath-hold maneuver under similar conditions as the subject. In an embodiment, the compromised cerebrovascular reactivity is indicative of Alzheimer's disease.

In an embodiment, the transcranial Doppler signals are acquired in response to insonation of a basal cerebral artery. In an embodiment, the method includes the steps of fixing a transcranial Doppler transducer on a temporal window of the subject using a fixation device. In an embodiment, the method further includes the steps of adjusting a target depth of the transcranial Doppler transducer to an estimated expected depth for a middle cerebral artery of the subject, and determining an optimal strong signal by adjustment of the depth and transducer position. In an embodiment, the breath-hold maneuver is performed by the subject for a predetermined breath-hold (BH) time or until the subject needs to exhale. In an embodiment, the cardiac measurements are heartbeats.

Disclosed is a method of treatment of preclinical Alzheimer's disease in a subject. The method includes the steps of acquiring a set of transcranial Doppler signals from a subject during performance of a breath-hold maneuver by the subject and calculating cerebral blood flow velocity (CBFV) measurements in response to the set of transcranial Doppler signals; acquiring a set of cardiac measurements of the subject during performance of the breath-hold maneuver, wherein the set of cardiac measurements include systolic velocity (Vs) and diastolic velocity (Vd) in each cardiac cycle for cardiac cycles during the breath-hold maneuver; calculating, using a processor, a mean velocity by averaging the CBFV measurements within each cardiac cycle; calculating, using the processor, a breath-hold acceleration index based on a linear regression correlation of temporal variations of the mean velocity across all cardiac cycles during the breath-hold maneuver; detecting presence of preclinical Alzheimer's disease in the subject in response to a breath-hold acceleration index of the subject being more than one standard deviation less than a breath-hold acceleration index of a healthy individual performing breath-hold maneuver under similar conditions as the subject; and administering a therapeutically effective compound to the subject detected of having preclinical Alzheimer's disease. In an embodiment, the therapeutically effective compound is an anti-amyloid agent. In an embodiment, the therapeutic compound is solanezumab or verubecestat or aducanumab. In an embodiment, the transcranial Doppler signals are acquired in response to insonation of a basal cerebral artery. In an embodiment, the method further includes the steps of fixing a transcranial Doppler transducer on a temporal window of the subject using a fixation device. In an embodiment, the method further includes the steps of adjusting a target depth of the transcranial Doppler transducer to an estimated expected depth for a middle cerebral artery of the subject, and determining an optimal strong signal by adjustment of the depth and transducer position. In an embodiment, the breath-hold maneuver is performed by the subject for a predetermined breath-hold (BH) time or until the subject needs to exhale.

Disclosed is a method of treating compromised cerebrovascular reactivity in a subject. The method includes the steps of: acquiring a set of transcranial Doppler signals from a subject during performance of a breath-hold maneuver by the subject and calculating cerebral blood flow velocity (CBFV) measurements in response to the set of transcranial Doppler signals; acquiring a set of cardiac measurements of the subject during performance of the breath-hold maneuver, wherein the set of cardiac measurements include systolic velocity (Vs) and diastolic velocity (Vd) in each cardiac cycle for cardiac cycles during the breath-hold maneuver; calculating, using a processor, a mean velocity by averaging the CBFV measurements within each cardiac cycle; calculating, using the processor, a breath-hold acceleration index based on a linear regression correlation of temporal variations of the mean velocity across all cardiac cycles during the breath-hold maneuver; detecting presence of compromised cerebrovascular reactivity in the subject in response to a breath-hold acceleration index of the subject being more than one standard deviation less than a breath-hold acceleration index of a healthy individual performing breath-hold maneuver under similar conditions as the subject; and administering a therapeutically effective compound to the subject, along with providing a behavioral modification regimen, in response to detecting compromised cerebrovascular reactivity in the subject. In an embodiment, the therapeutically effective compound is one or more of an acetylcholinesterase inhibitor, a glutamate modulator, and an anti-amyloid agent. In an embodiment, the behavioral modification regimen is one or more of exercise, psychotherapy, cognitive retraining, and skills training to regain cognitive functions.

Any aspect or embodiment described herein can be combined with any other aspect or embodiment as disclosed herein. While the disclosure has been described in conjunction with the detailed description thereof, the drawings and detailed description are intended to illustrate and not limit the scope of the disclosure, which is defined by the scope of the appended claims. Other aspects, advantages, and modifications are within the scope of the following claims.

BRIEF DESCRIPTION OF THE DRAWINGS

The patent or application file contains at least one drawing executed in color. Copies of this patent or patent application publication with color drawing(s) will be provided by the Patent Office upon request and payment of the necessary fee.

The present disclosure can be better understood by referring to the following figures.

FIG. 3A is an illustration of the TCD envelope waveforms obtained during the breath-holding (BH) experiment. The two vertical lines indicate the beginning and the end of the breath-holding maneuver. FIG. 3B is an illustration of the Mean velocity ($V_m$) calculated by averaging the envelope waveform samples (FIG. 3A) within each cardiac cycle, $V_{(m)max}$ is a maximum mean blood flow velocity during breath-holding. FIG. 3C is a graphical representation of the slope of eight successive sets of data points plotted against time, where the maximum R-value (BHAI=Breath-Hold Acceleration Index) occurred.

FIG. 5A is a graphical representation of mean velocity (Vm) plotted against time; the eight data points shown are from the location of the most linear portion of the Vm change during the breath-holding maneuver, when the subject is at a 15 degree-head-down tilt (HDT). FIG. 5B is a graphical representation of the regression line from Vm plotted against cardiac cycle; the circles are the same as in FIG. 5A. FIG. 5C is a graphical representation of mean velocity (Vm) plotted against time; the eight data points shown are from the location of the most linear portion of the Vm change during the breath-holding maneuver, when the subject is at a 15 degree-head-up tilt (HDT). FIG. 5D is a graphical representation of the regression line from Vm plotted against cardiac cycle; the circles are the same as in FIG. 5C. FIG. 5E is a graphical representation of mean velocity (Vm) plotted against time; the eight data points shown are from the location of the most linear portion of the Vm change during the breath-holding maneuver, when the subject is at a 30 degree-HUT. FIG. 5F is a graphical representation of the regression line from Vm plotted against cardiac cycle; the circles are the same as in FIG. 5E. FIG. 5G is a graphical representation of mean velocity (Vm) plotted against time; the eight data points shown are from the location of the most linear portion of the Vm change during the breath-holding maneuver, when the subject is at a 45 degree-HUT. FIG. 5H is a graphical representation of the regression line from Vm plotted against cardiac cycle; the circles are the same as in FIG. 5G.

DETAILED DESCRIPTION

Figure 1:
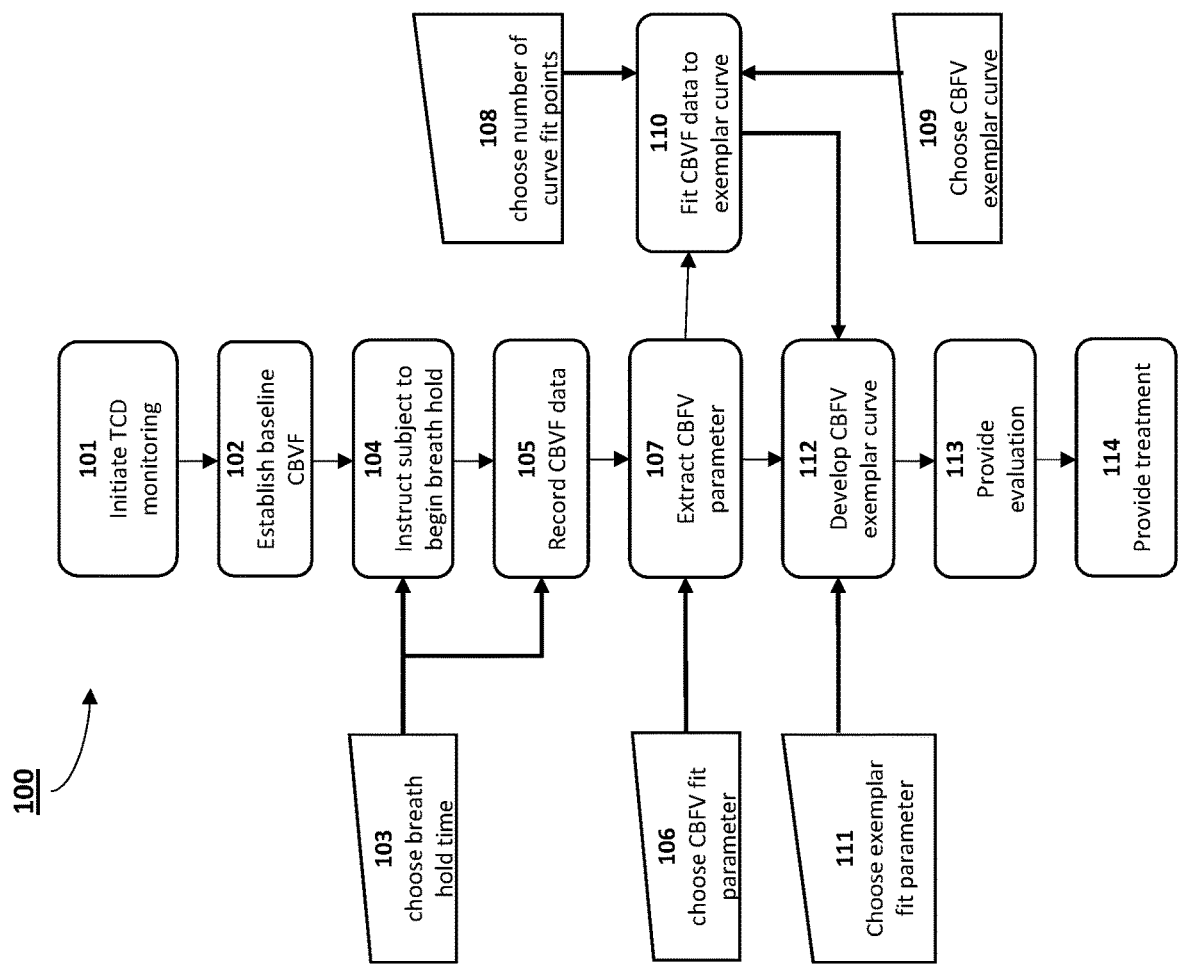
FIG. 1 is a schematic representation of a method of evaluating CBFV using a TCD device, according to an embodiment.

The social and economic burden due to Alzheimer's disease constitute an enormous problem. None of the pharmacologic treatments currently available for Alzheimer's disease stops or even slows the progression of the disease. Research on effective treatments of Alzheimer's disease is hindered by the fact that Alzheimer's disease begins to develop 10 to 20 years before showing any symptoms of cognitive decline. This pre-symptomatic period is called preclinical Alzheimer's disease. As with cardiac disease, cancer, and many other diseases, early detection and diagnosis are critical. The earlier medical treatment can be started in these diseases, the more likely a positive outcome. Thus, a logical strategy for addressing Alzheimer's disease should be the same—i.e., to look for early signs of Alzheimer's disease and test if therapeutics are effective. This strategy requires identifying reliable and accurate biomarkers of Alzheimer's disease that can differentiate normal aging from preclinical Alzheimer's disease.

Based on a hypothetical model of dynamic biomarkers of Alzheimer's disease proposed by the National Institute of Aging (NIA), amyloid-β (Aβ) accumulation in the brain is the first event in preclinical Alzheimer's disease that precedes other pathologic changes and the eventual development of dementia, termed Alzheimer's disease with dementia. Aβ is a peptide predominating amyloid plaques found in the brains of Alzheimer's disease patients. For several years, researchers have studied the concentration and accumulation onset of Aβ in the brain. However, current techniques to detect Aβ accumulation are invasive (cerebrospinal fluid analysis) or expensive (amyloid PET scans) and thus have limited accessibility as frontline screening and diagnostic tools for Alzheimer's disease. It has been established that cerebral hypoperfusion and increased pulsatility index are associated with a clinical diagnosis of Alzheimer's disease. Changes in cerebral perfusion are present long before clinical symptoms of Alzheimer's disease are manifest. Cerebral perfusion is much easier to assess than Aβ accumulation. Cerebral perfusion is the process by which arterial blood is delivered to capillary beds in brain tissue. CVR, the ability of cerebral vessels to dilate or constrict, is an excellent tool to evaluate cerebral perfusion. CVR can be quantified in vivo using transcranial Doppler (TCD). TCD is a noninvasive sensing modality that measures blood flow velocities (CBFV) in cerebral arteries with high temporal resolution. CVR measures the increase in CBFV resulting from a $CO_2$ vasodilatory stimulus, often using BHI. The BHI is the maximum percentage increase in CBFV divided by a set breath-holding time, which is usually 30 seconds. BHI suffers from low reproducibility and high variability. BHAI was used to assess CVR using a breath-holding maneuver. BHAI is obtained by linear regression of the most linear portion of CBFV increase during the breath-hold maneuver. This index has less variability when compared with the conventional BHI measure and is easy to implement as a frontline tool for detection of preclinical Alzheimer's disease and staging the patient for appropriate treatment.

Asymptomatic Alzheimer's disease characterized by neuropathologic (Aβ) changes precede the onset of symptoms by ten or more years. Cerebrovascular reactivity (CVR) is a strong indicator of cerebrovascular damage. CVR can be quantified by measuring changes in CBFV resulting from a $CO_2$ vasodilatory stimulus, often using BHI. In this method, TCD ultrasound is used to measure CBFV changes in the middle cerebral artery during a breath-hold maneuver. The BHI method can be refined by recording mean arterial pressure (MAP) and end-tidal $CO_2$, but these additional measurements make BHI more complex and less convenient. Despite the variability of BHI, there is a significant linear relationship between CBF and $PaCO_2$ within physiological limits. Additionally, CBF and CBFV have an excellent correlation in response to hypercapnia.

A robust method was developed to exploit the linear relationship between $PaCO_2$ and CBFV to measure CVR using the breath-holding maneuver. Using CVR, BHAI was calculated that provides an indication of cognitive or pathologic impairment of brain activity. This method combines the breath-holding maneuver and the linear relationship of CBF and $PaCO_2$ along with the breath-holding technique to develop an alternative index—breath-hold acceleration index (BHAI)—to evaluate CVR that is more accurate and reliable. This new index was obtained by linear regression of the most linear portion of the mean velocity change during the breath-hold maneuver. The regression represents acceleration (change in blood flow velocity per unit of time) sampled at each cardiac cycle. This method was also not affected by the body position of the subject on CVR values. BHAI has less variability in comparison with the conventional standard BHI. Methods disclosed here demonstrate that impaired CVR precedes symptomatic Alzheimer's disease, and that preclinical Alzheimer's disease subjects identified as having normal cognition and function (CDR=0) but with elevated-Aβ (Aβ+) have impaired CVR detectable by BHAI measurement.

A "therapeutically effective compound" as provided herein refers to a compound in an amount effective to achieve any indicia of success in the treatment or amelioration of compromised cerebrovascular reactivity. In one aspect, the disclosure provides methods for treating a subject having preclinical or asymptomatic Alzheimer's disease or Alzheimer's disease. The indicia of success in the treatment or amelioration of compromised cerebrovascular reactivity is measured by any objective or subjective parameter such as abatement; remission; diminishing of symptoms or making the injury, disease, or condition more tolerable to the subject; slowing in the rate of degeneration or decline (e.g., improved cognition or memory); making the final point of degeneration less debilitating; and/or improving a subject's physical or mental well-being. The administration of pharmaceutical compositions of the disclosure may or can lead to the elimination of a sign or symptom, however, elimination is not required. In one aspect, the disclosure provides methods for treating a subject having preclinical or asymptomatic Alzheimer's disease following detection of disease based on BHAI. The actual amount effective for a particular application will depend, inter alia, on the condition being treated. When administered in methods to treat a disease, the pharmaceutical compositions described herein will contain an active compound (e.g., an anti-amyloid agent) to achieve the desired result, e.g., reducing, eliminating, or slowing the progression of disease symptoms of Alzheimer's disease. The effect can be detected by any assay method known in the art, including BHAI. The precise effective amount for a subject will depend upon the subject's body weight, size, and health; the nature and extent of the condition; and the composition or combination of compositions selected for administration.

Disclosed is a method of detecting compromised cerebrovascular reactivity in a subject. The method includes the steps of acquiring a set of transcranial Doppler signals from a subject during performance of a breath-hold maneuver by the subject and calculating cerebral blood flow velocity (CBFV) measurements in response to the set of transcranial Doppler signals; acquiring a set of cardiac measurements of the subject during performance of the breath-hold maneuver, wherein the set of cardiac measurements include systolic velocity (Vs) and diastolic velocity (Vd) in each cardiac cycle for cardiac cycles during the breath-hold maneuver; calculating, using a processor, a mean velocity by averaging the CBFV measurements within each cardiac cycle; calculating, using the processor, a breath-hold acceleration index based on a linear regression correlation of temporal variations of the mean velocity across all cardiac cycles during the breath-hold maneuver; and detecting presence of compromised cerebrovascular reactivity in the subject in response to a breath-hold acceleration index of the subject being more than one standard deviation less than a breath-hold acceleration index of a healthy individual performing breath-hold maneuver under similar conditions as the subject. In an embodiment, the compromised cerebrovascular reactivity is indicative of preclinical Alzheimer's disease. In an embodiment, the compromised cerebrovascular reactivity is indicative of Alzheimer's disease in response to the breath-hold acceleration index of the subject being more than two standard deviations less than a breath-hold acceleration index of a healthy individual performing breath-hold maneuver under similar conditions as the subject. In an embodiment, the method further comprises the step of calculating, using the processor, a pulsatility index for each cardiac cycle during the breath-hold maneuver, wherein the pulsatility index is the quotient when the difference in the systolic velocity (Vs) and diastolic velocity (Vd) in each cardiac cycle is divided by the mean velocity; detecting presence of compromised cerebrovascular reactivity in the subject in response to an increased pulsatility index and a breath-hold acceleration index of the subject being more than one standard deviation less than a breath-hold acceleration index of a healthy individual performing breath-hold maneuver under similar conditions as the subject. In an embodiment, the compromised cerebrovascular reactivity is indicative of Alzheimer's disease.

In an embodiment, the transcranial Doppler signals are acquired in response to insonation of a basal cerebral artery. In an embodiment, the method includes the steps of fixing a transcranial Doppler transducer on a temporal window of the subject using a fixation device. In an embodiment, the method further includes the steps of adjusting a target depth of the transcranial Doppler transducer to an estimated expected depth for a middle cerebral artery of the subject, and determining an optimal strong signal by adjustment of the depth and transducer position. In an embodiment, the breath-hold maneuver is performed by the subject for a predetermined breath-hold (BH) time or until the subject needs to exhale. In an embodiment, the cardiac measurements are heartbeats.

In an embodiment, the mean coefficient of variation was 43.7% lower in BHAI in comparison with BHI. Neither index showed statistical significance in CVR based on change in body position (P>0.05). BHAI is a more reliable measure of CVR. This method was successful in utilizing TCD measurements to screen for patients with asymptomatic Alzheimer's disease. In an embodiment, a patient who tests positive for asymptomatic Alzheimer's disease is prescribed a therapeutically effective compound. In an embodiment, a patient who tests positive for asymptomatic Alzheimer's disease is prescribed an anti-amyloid treatment or management regimen. In an embodiment, the anti-amyloid treatment regimen includes solanezumab or verubecestat or aducanumab. In an embodiment, the anti-amyloid treatment regimen includes a beta-secretase inhibitor. In an embodiment, a patient who tests positive for asymptomatic Alzheimer's disease is prescribed Razadyne® (galantamine), Exelon® (rivastigmine), Aricept® (donepezil), Namenda® (memantine), or combinations thereof.

An embodiment of a method of treatment of preclinical Alzheimer's disease in a subject includes the steps of acquiring a set of transcranial Doppler signals from a subject during performance of a breath-hold maneuver by the subject and calculating cerebral blood flow velocity (CBFV) measurements in response to the set of transcranial Doppler signals; acquiring a set of cardiac measurements of the subject during performance of the breath-hold maneuver, wherein the set of cardiac measurements include systolic velocity (Vs) and diastolic velocity (Vd) in each cardiac cycle for cardiac cycles during the breath-hold maneuver; calculating, using a processor, a mean velocity by averaging the CBFV measurements within each cardiac cycle; calculating, using the processor, a breath-hold acceleration index based on a linear regression correlation of temporal variations of the mean velocity across all cardiac cycles during the breath-hold maneuver; detecting presence of preclinical Alzheimer's disease in the subject in response to a breath-hold acceleration index of the subject being more than one standard deviation less than a breath-hold acceleration index of a healthy individual performing breath-hold maneuver under similar conditions as the subject; and administering a therapeutically effective compound to the subject detected of having preclinical Alzheimer's disease. In an embodiment, the therapeutically effective compound is an anti-amyloid agent. In an embodiment, the therapeutic compound is solanezumab or verubecestat or aducanumab. In an embodiment, the transcranial Doppler signals are acquired in response to insonation of a basal cerebral artery. In an embodiment, the method further includes the steps of fixing a transcranial Doppler transducer on a temporal window of the subject using a fixation device. In an embodiment, the method further includes the steps of adjusting a target depth of the transcranial Doppler transducer to an estimated expected depth for a middle cerebral artery of the subject, and determining an optimal strong signal by adjustment of the depth and transducer position. In an embodiment, the breath-hold maneuver is performed by the subject for a predetermined breath-hold (BH) time or until the subject needs to exhale.

Provided here are methods of detecting asymptomatic Alzheimer's disease in a patient by TCD monitoring and calculation of BHAI. In an embodiment of a method 100 as shown in FIG. 1, TCD monitoring is initiated (step 101). In an embodiment, low-frequency (<2 MHz) ultrasound waves are used to insonate the basal cerebral arteries through specific regions of the skull (acoustic windows). A more commonly used acoustic window is the transtemporal window, which is located above the zygomatic ridge between the lateral canthus of the eye and auricular pinna. This window is used to transmit ultrasound waves to the middle (MCA), anterior (ACA), posterior cerebral arteries (PCA), and terminal internal carotid artery (ICA). The target artery is insonated by selecting an appropriate acoustic window, probe angle, and sample volume depth. The probe angle and volume depth are slowly simultaneously varied by manual adjustment of the transducer, until the strongest velocity spectrum is seen on a monitor.

The ultrasound probe can be fixed in a headset or manually applied to a patient. In an embodiment. a commercial machine (Doppler BoxX, Compumedics Germany Gmbh) is used to collect CBFV measurements. In an embodiment, the TCD transducer was fixed on the temporal window using a custom fixation device. In an embodiment, the depth was initially set to expected depths for the middle cerebral artery, and the strongest signal was found by manual adjustment of the depth and transducer position. Once the signal was optimized, the transducer was locked in place.

Next, in step 102, a CBFV baseline was established, i.e., the blood flow conditions before the test. A breath-hold (BH) time is chosen. In an embodiment, as shown in step 103, a BH time is manually chosen. In an embodiment, the BH time is 30 seconds. In an embodiment, BH time is as long as the subject is able. BH times can range from about 10 to 40 seconds. The subject is instructed to hold his breath for as long as the BH time or as long as they are able, whichever comes first (step 104). The CBFV data is continually measured and recorded during the test (step 105). After the BH, CBFV data continues to be recorded for at least another few minutes. A CBFV fit parameter is chosen. In an embodiment, as shown in step 106, a CBFV fit parameter is manually chosen. In an embodiment, as shown in step 107, the CBFV parameter is extracted from the recorded CBVF data. CBFV parameters can be one or more of maximum systolic velocity, minimum end-diastolic velocity, pulsatility index, and resistive index. In an embodiment, the fit parameter is the mean value of CBFV per heartbeat, i.e., between the end-diastolic points from heartbeat to heartbeat. A number of curve fit points are chosen (step 108). The choice of number of curve points is made with respect to an expected physiological response time. This depends upon the rate of the CBFV fit parameter. For example, the human heart rate is roughly 1.0-1.6 beats/second. If a response time of about 6 seconds is desired to be observed, curve fit points between (6 seconds)(1.0 beats/second)-(6 seconds)(1.6 beats/second) is used, or between about 6 and 10 fit points. In an embodiment, this number is eight. A CBFV exemplar curve is chosen (step 109). This curve is chosen based on physiology expectations. The CBFV data is fitted to an exemplar curve (step 110), given a number of curve fit points (step 108). For example, the number of curve fit points is 8. In an example, the exemplar curve is a CBFV exemplar curve (step 109). In the example, this curve is a linear curve, as it is expected that CBFV increases during a breath hold. An exemplar fit parameter is chosen (step 111). In the example, the exemplar fit parameter is the linear fit (the best-fit slope) of the eight points. The slope of the points in the example has units of velocity change per time, which is the same as acceleration. The CBFV data—exemplar curve fit is performed on each window of curve fit points (step 112) (in an embodiment, for every eight points). The window of points with the best fit to the exemplar curve is found. In an embodiment, the "best fit" means the highest Pearson's correlation coefficient (or R-value). Other techniques for goodness-of-fit include sum of squares due to error (SSE) and root mean squared error (RMSE).

The exemplar fit parameter is used in diagnosis and/or evaluation (step 113). The parameter is compared to research establishing norms and variance. A result further away from the mean a certain number of standard deviations would be considered abnormal. In an embodiment, a BHAI result much less than one standard error measurement (about 0.3 m/s/s) than a healthy average (about 1.25 m/s/s) indicates compromised cerebrovascular reactivity and warrant further medical evaluation and treatment (step 114).

Figure 2:
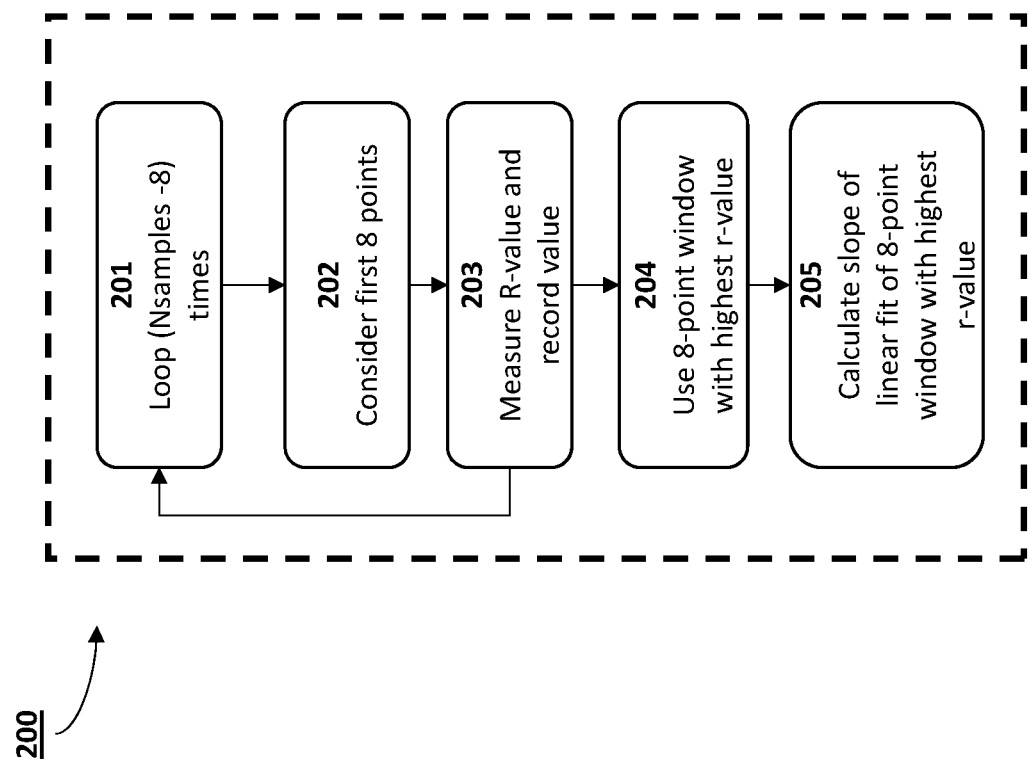
FIG. 2 is a schematic representation of a method for fitting the CBFV data to an exemplar curve (step 110 in FIG. 1), given a number of curve fit points (step 108 in FIG. 1). For example, the number of curve fit points is 8. In an example, the exemplar curve is a CBFV exemplar curve (step 109 in FIG. 1). And in an example, the CBFV exemplar curve is linear.

The method 200 as shown in FIG. 2 is directed to a method for fitting the CBFV data to an exemplar curve (step 110 in FIG. 1), given a number of curve fit points (step 108 in FIG. 1). For example, the number of curve fit points is 8. In an example, the exemplar curve is a CBFV exemplar curve (step 109 in FIG. 1). And in an example, the CBFV exemplar curve is linear. In step 201, the steps 203-205 are set to be performed in a loop as many as times as set based upon the number of samples and number of curve fit points. In step 202, the number of curve fit points is considered. In step 203, the r-value is measured and recorded. In step 204, the highest Pearson's correlation coefficient (or R-value) is determined using the 8-point window. In step 205, the slope of linear fit of the 8-point window with highest r-value is calculated.

In another embodiment, BHAI can be used to distinguish normal aging subjects from preclinical Alzheimer's disease subjects with high statistical significance. For example, the CVR was evaluated in three groups: (i) healthy control subjects who had a Clinical Dementia Rating (CDR) score of 0 and did not have elevated amyloid-β (Aβ) on amyloid PET imaging, (ii) preclinical Alzheimer's disease subjects had CDR=0 with elevated Aβ, and (iii) prodromal to mild Alzheimer's disease subjects had CDR scores of 0.5 or higher and elevated Aβ. CVR was calculated using two indices: the conventional BHI and the new BHAI. TCD parameters between the control group, group with Alzheimer's disease, and group with preclinical Alzheimer's disease were compared. CVR was significantly decreased in preclinical, prodromal, and mild Alzheimer's disease subjects as compared to the healthy group. Lower CVR in the preclinical Alzheimer's disease group was detected using the BHAI index but not the conventional BHI index. BHAI was able to distinguish normal aging and preclinical subjects with high statistical significance (p<0.001). BHI and pulsatility index were able only to distinguish Alzheimer's disease from healthy and preclinical subjects (p<0.001).

An embodiment of a method includes the steps of determining BHAI in a subject and detecting a cognitive impairment in the subject depending on the extent of the decrease of BHAI in the subject as compared to the BHAI of a healthy group of individuals, such as normal aging subjects. In certain embodiments, this method includes the step of treating the subject with cognitive impairment with one or more of behavioral modification regimens, environmental modifications, and therapeutically effective compounds. Therapeutically effective compounds can include one or more of acetylcholinesterase inhibitors, glutamate modulators, antipsychotic medications, anti-anxiety medications, or antidepressant medications. Behavioral modification regimens can include one or more of art, music, exercise, psychotherapy, orientation exercises, cognitive retraining, and skills training to regain cognitive functions.

An embodiment of a method includes the steps of determining BHAI in a subject and detecting dementia in the subject depending on the extent of the decrease of BHAI in the subject as compared to the BHAI of a healthy group of individuals, such as normal aging subjects. In certain embodiments, this method includes the treatment of the subject with dementia with one or more of behavioral modification regimens, environmental modifications, and therapeutically effective compound.

An embodiment of a method of classifying subjects for a clinical trial for subjects with preclinical Alzheimer's disease or asymptomatic Alzheimer's disease. The method includes the steps of obtaining BHAI of the subject, comparing the level(s) of the BHAI and behavior of the subject to the BHAI and behaviors of a healthy group of individuals, and determining that subject is appropriate for a clinical trial to evaluate a behavioral modification regimen, environmental modification, therapeutically effective compound, or combinations thereof, when the presence of a decreased level of BHAI and/or altered behavior indicates that the subject has an elevated likelihood of having preclinical Alzheimer's disease or asymptomatic Alzheimer's disease.

An embodiment of a method of treating compromised cerebrovascular reactivity in a subject includes the steps of: acquiring a set of transcranial Doppler signals from a subject during performance of a breath-hold maneuver by the subject and calculating cerebral blood flow velocity (CBFV) measurements in response to the set of transcranial Doppler signals; acquiring a set of cardiac measurements of the subject during performance of the breath-hold maneuver, wherein the set of cardiac measurements include systolic velocity (Vs) and diastolic velocity (Vd) in each cardiac cycle for cardiac cycles during the breath-hold maneuver; calculating, using a processor, a mean velocity by averaging the CBFV measurements within each cardiac cycle; calculating, using the processor, a breath-hold acceleration index based on a linear regression correlation of temporal variations of the mean velocity across all cardiac cycles during the breath-hold maneuver; detecting presence of compromised cerebrovascular reactivity in the subject in response to a breath-hold acceleration index of the subject being more than one standard deviation less than a breath-hold acceleration index of a healthy individual performing breath-hold maneuver under similar conditions as the subject; and administering a therapeutically effective compound to the subject, along with providing a behavioral modification regimen, in response to detecting compromised cerebrovascular reactivity in the subject. In an embodiment, the therapeutically effective compound is one or more of an acetylcholinesterase inhibitor, a glutamate modulator, and an anti-amyloid agent. In an embodiment, the behavioral modification regimen is one or more of exercise, psychotherapy, cognitive retraining, and skills training to regain cognitive functions.

An embodiment of a method includes the steps of determining BHAI in a subject who has been treated with one or more of behavioral modification regimens, environmental modifications, and therapeutically effective compounds. This method includes the step of monitoring the efficacy of the behavioral modification regimen, environmental modification, therapeutically effective compound, or combinations thereof by periodically evaluating the BHAI of the subject. This method can optionally include the step of maintaining or changing the behavioral modification regimen, environmental modification, therapeutically effective compound, or combinations thereof based on the changes to the BHAI of the subject during the periodical evaluation.

Disclosed herein, in certain embodiments, is a non-transitory computer-readable medium with instructions stored thereon, that when executed by a processor, perform the steps to provide a clinical decision support system for detecting patients with compromised cerebrovascular reactivity. The instructions cause at least one processor to perform the following steps: receiving a plurality of transcranial Doppler signals from a subject during performance of a breath-hold maneuver by the subject and calculating cerebral blood flow velocity (CBFV) measurements in response to the set of transcranial Doppler signals; acquiring a set of cardiac measurements of the subject during performance of the breath-hold maneuver, wherein the set of cardiac measurements include systolic velocity (Vs) and diastolic velocity (Vd) in each cardiac cycle for cardiac cycles during the breath-hold maneuver; calculating a mean velocity by averaging the CBFV measurements within each cardiac cycle; calculating a BHAI based on a linear regression correlation of temporal variations of the mean velocity across all cardiac cycles during the breath-hold maneuver; and providing the BHAI along with other clinical information about the subject to an electronic interface. In an embodiment, the instructions further cause at least one processor to perform the following steps: calculating a pulsatility index for each cardiac cycle during the breath-hold maneuver, wherein the pulsatility index is the quotient when the difference in the systolic velocity (Vs) and diastolic velocity (Vd) in each cardiac cycle is divided by the mean velocity; and providing the pulsatility index and BHAI along with other clinical information about the subject to an electronic interface.

In certain embodiments, the non-transitory computer-readable medium includes volatile and non-volatile memory devices. In certain embodiments, the processor includes an Intel or AMD x86 based single or multi-core central processing unit (CPU), an ARM processor, or similar computer processor for processing the data. In some cases, the CPU or microprocessor is any conventional general purpose single- or multi-chip microprocessor such as an Intel Pentium processor, an Intel 8051 processor, a RISC or MISS processor, a Power PC processor, or an ALPHA processor. In some cases, the microprocessor is any conventional or special purpose microprocessor such as a digital signal processor or a graphics processor. The microprocessor typically has conventional address lines, conventional data lines, and one or more conventional control lines. As described below, the software according to the various embodiments of the invention is executed on dedicated system or on a general purpose computer having a DOS, CPM, Windows, Unix, Linix or other operating system. In some instances, the system includes non-volatile memory, such as disk memory and solid state memory for storing computer programs, software and data and volatile memory, such as high speed ram for executing programs and software.

In some embodiments, a computer-readable medium refers to any storage device used for storing data accessible by a computer, as well as any other means for providing access to data by a computer. Examples of a storage device-type computer-readable medium include a magnetic hard disk, an optical disk, such as a CD-ROM and a DVD, a magnetic tape, or a memory chip. Computer-readable physical storage media useful in various embodiments can include any physical computer-readable storage medium, e.g., solid state memory (such as flash memory), magnetic and optical computer-readable storage media and devices, and memory that uses other persistent storage technologies. In some embodiments, a computer readable media is any tangible media that allows computer programs and data to be accessed by a computer. Computer readable media can include volatile and nonvolatile, removable and non-removable tangible media implemented in any method or technology capable of storing information such as computer readable instructions, program modules, programs, data, data structures, and database information.

EXAMPLES

Examples below illustrate selected aspects of the methods disclosed here.

Example 1

Study Subjects.

Ten healthy, right-handed students were recruited from the University of Nebraska-Lincoln (UNL) (4 males, 6 females), with an average age of 21.4±1.7 years. The study was approved by the UNL Institutional Review Board and conducted in the Biomedical Signal & Signal Analysis laboratory at the University of Nebraska. Exclusion criteria included neurological diseases, pregnancy, consumption of alcohol within the last 24 hours, prior treatment for hypertension, diabetes, and cerebrovascular diseases. The participants were requested to attend a single session. They were notified of confidentiality, given a further explanation of their participation in the study, and surveyed with prescreening questions. All participants signed an informed consent form.

The TCD ultrasound basal examination was performed using a commercial machine (Doppler BoxX, Compumedics Germany Gmbh) to collect CBFV. The TCD transducer was fixed on the temporal window using a custom fixation device. For each subject, a proximal segment of the left (dominant hemisphere) middle cerebral artery was insonated at depths of 43-55 mm, with Doppler gate size between 8 and 10 mm. The transducers were 2 MHz pulsed-wave transducers. The depth was initially set to expected depths for the middle cerebral artery, and the strongest signal was found by manual adjustment of the depth and transducer position. Once the signal was optimized, the transducer was locked in place.

Breath-Hold Procedure.

The breath-hold procedure was adapted from Markus and Harrison (See, Markus H S, Harrison M J. Estimation of cerebrovascular reactivity using transcranial Doppler, including the use of breath-holding as the vasodilatory stimulus. Stroke 1992; 23:668-73). The subject was instructed to breathe normally until they were told to begin breath-holding following a normal inspiration. The subjects were instructed specifically not to begin their breath-hold by performing a Valsalva maneuver, but simply to stop breathing following inhalation and hold their breath for a maximum of 30 seconds or as long as they could before the need to inhale.

Experimental Setup and Procedures

CVR data were collected at five body positions using a tilt table (Essex 990, Ironman, China) customized to lock its angle of inclination at specific positions for measurement purposes. Participants were assisted onto the tilt table at a 30° head-up tilt (HUT) position, where initial TCD measurements were taken. After identification of the middle cerebral artery, the participants were asked to perform the breath-holding procedure in five positions, as follows: 45° HUT; 30° HUT; 15° HUT; supine position; and 15° head-down tilt (HDT). The order of each position and subsequent positions were assigned randomly. Throughout the experiment, the velocity envelope in the middle cerebral artery was recorded.

Data Processing.

Blood flow velocity data were recorded and then exported for further analysis in MATLAB (R2016b v. 8.4.0, Mathworks, Natick, MA, USA). The data were recorded unilaterally.

Figure 3A:
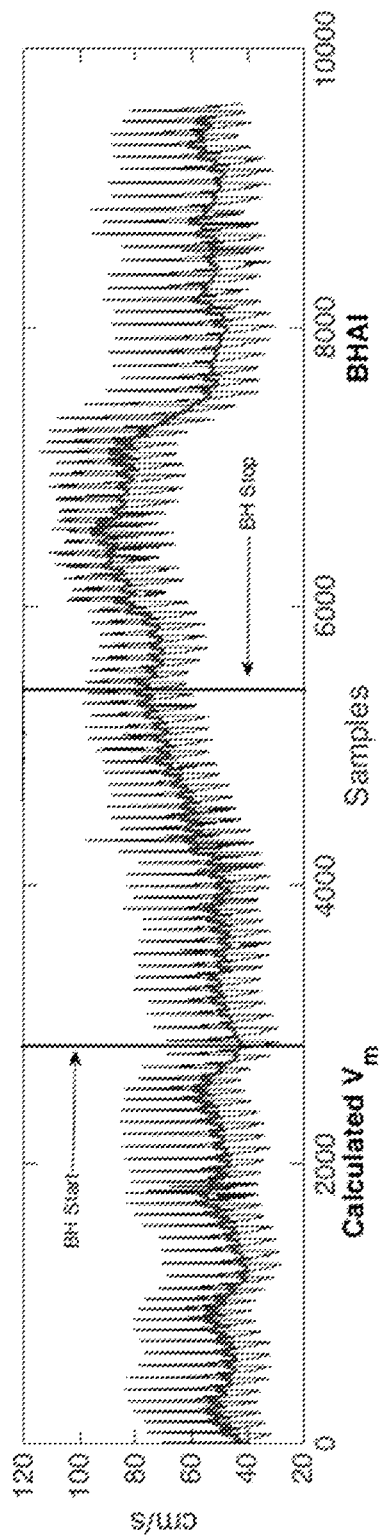
FIGS. 3A-3C illustrate the method of processing TCD measurements from a subject, according to an embodiment.
Figure 3B:
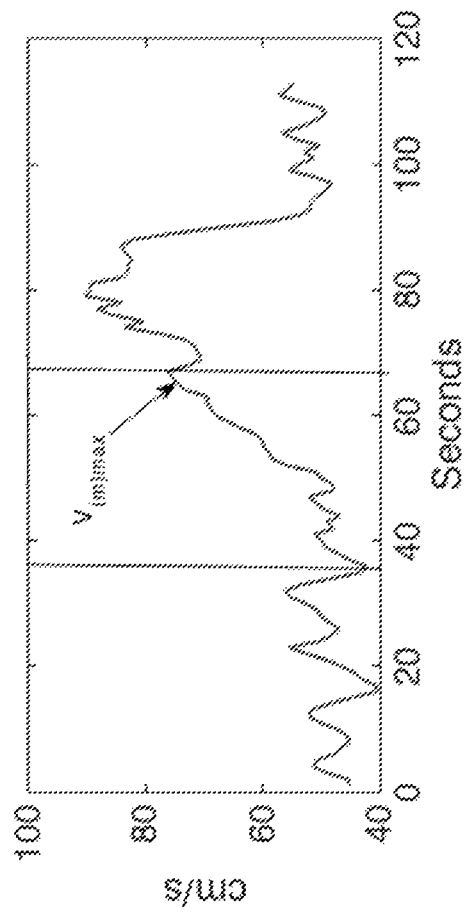
Figure 3C:
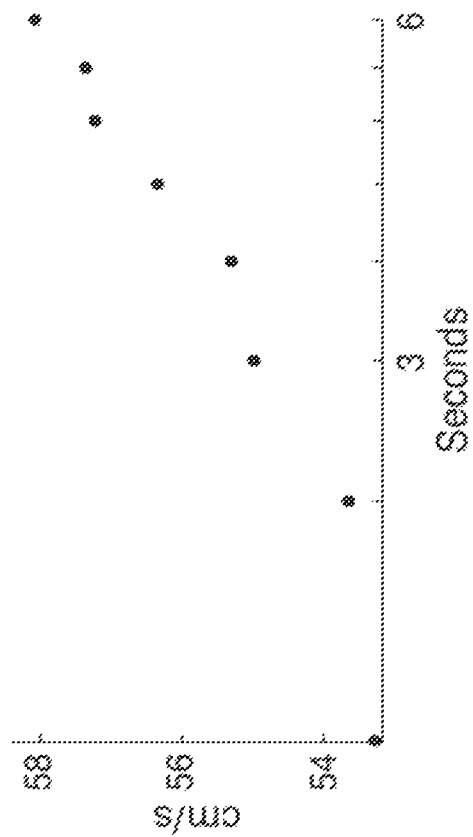

A customized MATLAB program was written for all processing of the TCD envelope waveforms obtained during the experiment. The TCD envelope waveform is a plot of the maximum velocity present in an artery versus time at a sampling rate of 100 samples per second (100 Hz). During the experiment, markers were recorded in the TCD waveform data to mark the beginning and the end of the breath-hold maneuver (FIG. 3A). FIGS. 3A-3C illustrate the method of processing TCD measurements from a subject, according to an embodiment. FIG. 3A is an illustration of the TCD envelope waveforms obtained during the breath-holding (BH) experiment. The two vertical lines indicate the beginning and the end of the breath-holding maneuver. Using these markers, 20-second segments from before and 30-second during the breath-holding maneuver were extracted from the envelope. The customized MATLAB program was used to detect the systolic velocity (Vs) and diastolic velocity (Vd) in each cardiac cycle. The mean velocity (Vm) was calculated by averaging the CBFV samples within each cardiac cycle (FIG. 3B) where each $V_i$ is an individual CBVF sample and N is the total number of samples in a cardiac cycle:

$$Vm = \frac{\sum_{i=1}^{N} Vi}{N}$$

The pulsatility index (PI) for each cardiac cycle was calculated as:

$$PI = \frac{(Vs - Vd)}{Vm}.$$

The PI of the middle cerebral artery is postulated to reflect the vascular resistance in the arteries distal from the location of acoustic insonation.

CVR was calculated using two methods. First, by using the standard BHI:

$$BHI = \frac{\frac{(V_{m,max} - V_{m,b})}{V_{m,b}}}{\Delta t}.$$

Vm,max is the maximum mean blood flow velocity during breath-holding, Vm,b is the average mean blood flow velocity before breath-holding, and Δt is the time from the beginning of breath-holding at which Vm,max occurs (usually 30 seconds). These velocities and time points can be seen in FIG. 3B. FIG. 3B is an illustration of the Mean velocity ($V_m$) calculated by averaging the envelope waveform samples (FIG. 3A) within each cardiac cycle, $V_{(m)max}$ is a maximum mean blood flow velocity during breath-holding.

BHAI is obtained by linear regression of the most linear portion of the Vm change during the breath-hold maneuver. The most linear portion of the breath-holding curve was determined by examining a succession of sample windows across time during the breath-hold, where each sample window consisted of eight consecutive data points of one cardiac cycle each. For each sample window, the Pearson's correlation coefficient (R-value) was calculated and stored. Then, the window was moved by one data point (one cardiac cycle) and the new R-value calculated and stored again. This process was repeated until the end of the breath-hold maneuver. The sample window that corresponded to the highest R-value was determined to be the most linear portion of the breath-holding curve. FIG. 3C is a graphical representation of the slope of eight successive sets of data points plotted against time, where the maximum R-value (BHAI=Breath-Hold Acceleration Index) occurred. BHAI was obtained by linear regression of the sample window, where the maximum R-value occurred (FIG. 3C).

Statistical Analyses.

The experiment followed a random-block analysis of a randomized complete block design with 10 subjects (blocks). Data were analyzed for BHI and BHAI separately. Analysis of variance for the randomized complete random-block design provided a test for the effect of angles to the values of BHI and BHAI. Estimated mean and the standard error were used to calculate the coefficient of variation (CV) for BHAI and BHI. CV was examined by a paired sample t-test. Statistical significance was set at $P<0.01$ for all statistical tests. Finally, a power analysis was conducted to visualize how the sample size affects the power of the test, and to calculate the sensitivity for BHI and BHAI. Sensitivity was defined as the minimum change in CVR value that BHI and BHAI indices can detect using 10 subjects; alpha was set to 0.05 and power was set to 0.8. All analyses were performed using SAS v 9.4 (SAS Institute Inc. headquartered in Cary, North Carolina, USA).

TABLE 1

Analysis of Variance (Type III Tests of Fixed Effects)

| Effect | BHAI (P-Value) | BHI (P-Value) |
|---|---|---|
| Angles | .27 (NS) | .92 (NS) |

NS = not significant;
BHAI = Breath-Hold Acceleration Index;
BHI = Breath-Holding Index.

To understand the interaction between body positions and CVR, 10 subjects performed the experiment in a tilt table. Results from BHAI and BHI analysis of variance were not statistically significant and are presented in Table 1. These results suggest that body position has no effect on CVR in young healthy subjects.

To compare between BHI and BHAI, least squares means and the standard error were estimated per angle. The mean CV was 43.7% lower in BHAI in comparison with BHI ($P<0.0001$) (Table 2). This result demonstrate that BHAI has higher precision and repeatability in comparison with the conventional standard (BHI). Finally, the average maximum R-value for BHAI was 0.966±03.

TABLE 2

Estimated Least Squares Mean for Each Angle.

| Angles | BHAI μ | BHAI SD | BHAI CV % | BHI μ | BHI SD | BHI CV % |
|---|---|---|---|---|---|---|
| −15 | 1.45 | .08 | 5.75 | 1.42 | .15 | 10.76 |
| 0 | 1.27 | .08 | 6.57 | 1.34 | .15 | 11.36 |
| 15 | 1.39 | .08 | 6.00 | 1.50 | .15 | 10.15 |
| 30 | 1.39 | .08 | 6.00 | 1.43 | .15 | 10.66 |
| 45 | 1.49 | .08 | 5.60 | 1.49 | .15 | 10.25 |

BHAI = Breath-Hold Acceleration Index; BHI = Breath-Holding Index; μ= Estimated Means; SD = Standard Error; CV = Coefficient of Variation.

Figure 4:
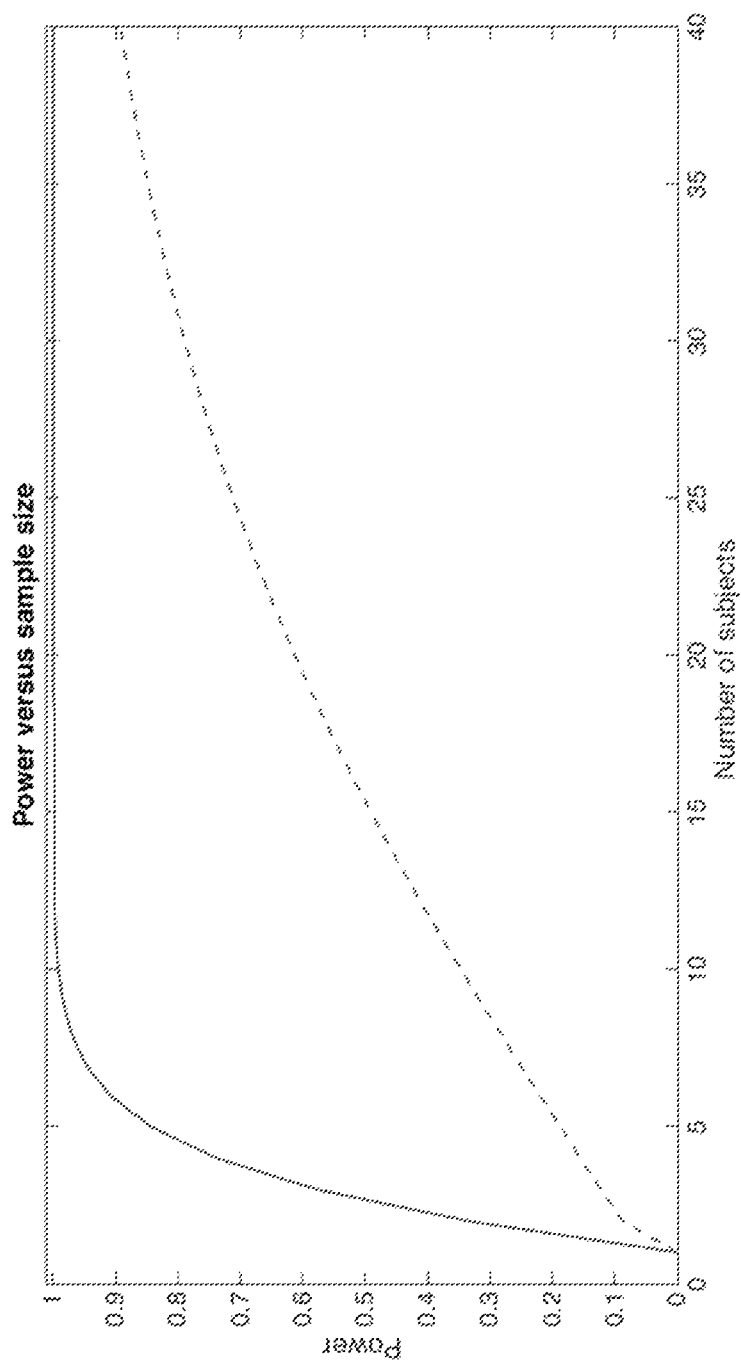
FIG. 4 is a graphical representation of the relationship between the number of subjects and the power of the test. BHAI is presented as the continuous line and BHI as the dotted line. The effect size values for BHAI and BHI were 0.22 cm/s$^2$ and 0.15 s$^{-1}$, respectively, and for both alpha was set to 0.05.

To compare the sensitivity, a power analysis was conducted using the 10 subjects to calculate the minimum detectable change in CVR for BHI and BHAI. The minimum detectable change for BHAI and BHI values were 0.14 cm/s² and 0.27 respectively, and the effect size values for BHAI and BHI were 0.22 cm/s² and 0.15 s⁻¹. Additionally, the relationship between sample size and the power of the test was examined for both BHI and BHA (FIG. 4). FIG. 4 is a graphical representation of the relationship between the number of subjects and the power of the test. BHAI is presented as the continuous line and BHI as the dotted line. The effect size values for BHAI and BHI were 0.22 cm/s² and 0.15 s⁻¹, respectively, and for both alpha was set to 0.05. These results demonstrate that the BHAI has higher sensitivity in comparison with the conventional standard (BHI).

BHAI was developed to assess CVR using a breath-hold maneuver. BHAI showed less variability and greater precision in comparison with the conventional BHI. Additionally, BHAI had a lower value of minimum detectable change in comparison with BHI. The minimum detectable change by itself is not enough to compare sensitivity because the two indices have different units. In this case, the effect size values for BHAI and BHI needed to be calculated and was higher in BHAI. The effect size values were calculated to represent the mean differences between supine position and 45° HUT. Using BHAI yielded larger effect size and smaller minimum detectable change in comparison with BHI. Thus, BHAI has more sensitivity in comparison with BHI. BHI average values were consistent with previously published large normative values (1.45 s$^{-1}$). BHAI was calculated using linear regression (slope) of the changes in CBFV with respect to cardiac cycle during a breath-hold maneuver.

Figure 5A:
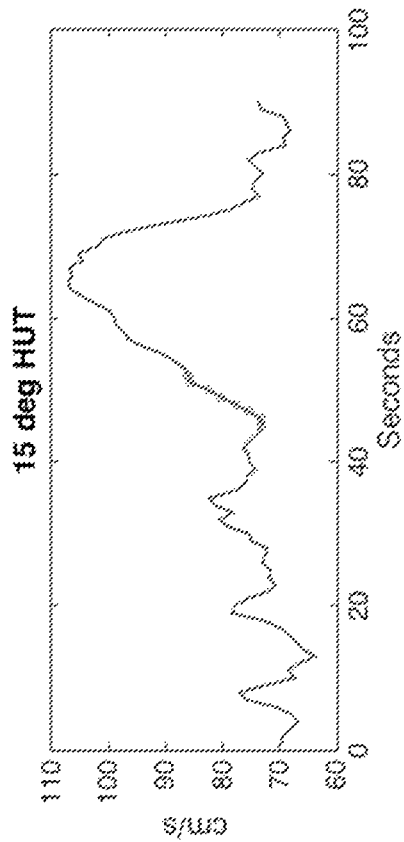
FIGS. 5A-5H are graphical representations of the plots of four different subjects in four different body positions.
Figure 5C:
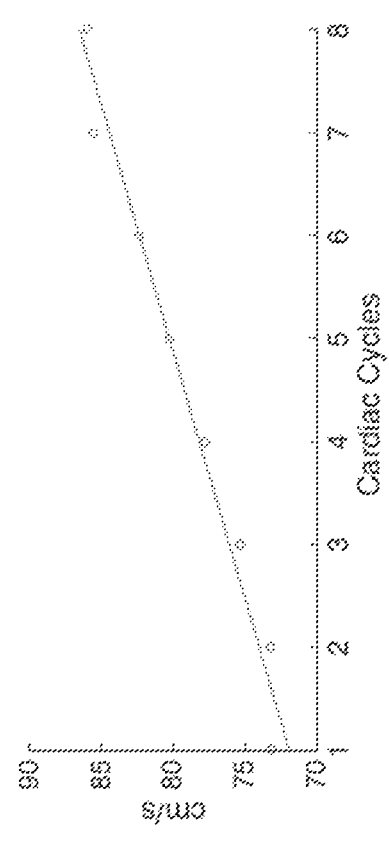
Figure 5B:
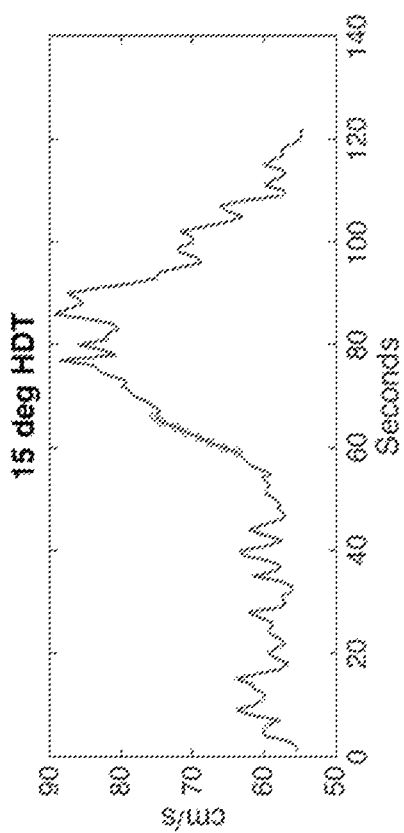
Figure 5D:
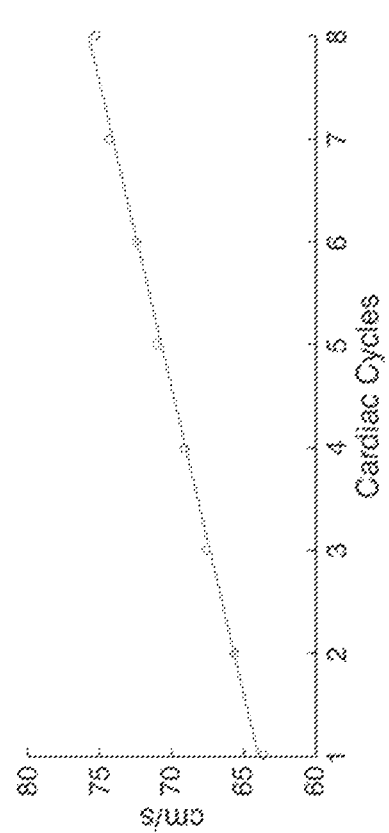
Figure 5E:
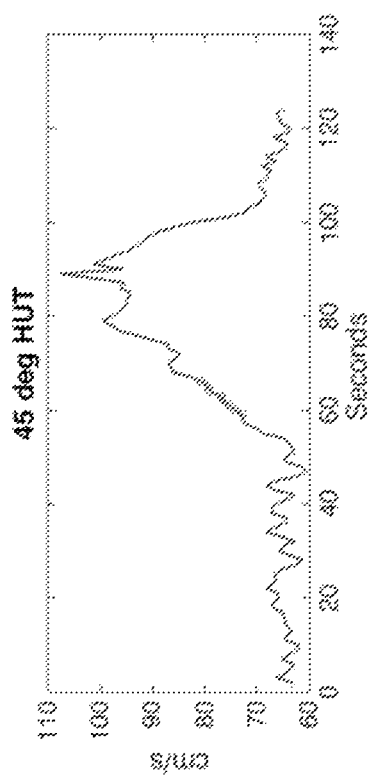
Figure 5F:
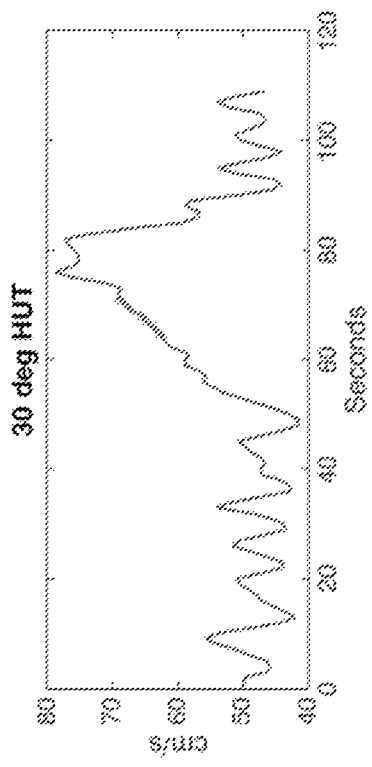
Figure 5G:
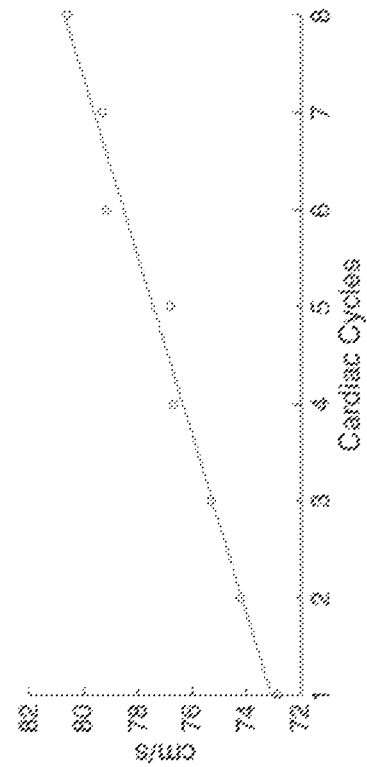
Figure 5H:
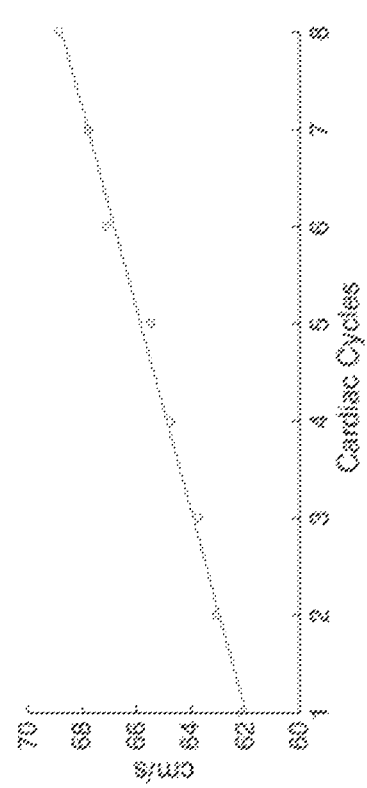

FIGS. 5A-5H are graphical representations of the plots of four different subjects in four different body positions. FIG. 5A is a graphical representation of mean velocity (Vm) plotted against time; the eight data points shown are from the location of the most linear portion of the Vm change during the breath-holding maneuver, when the subject is at a 15 degree-head-down tilt (HDT). FIG. 5B is a graphical representation of the regression line from Vm plotted against cardiac cycle; the circles are the same as in FIG. 5A. FIG. 5C is a graphical representation of mean velocity (Vm) plotted against time; the eight data points shown are from the location of the most linear portion of the Vm change during the breath-holding maneuver, when the subject is at a 15 degree-head-up tilt (HDT). FIG. 5D is a graphical representation of the regression line from Vm plotted against cardiac cycle; the circles are the same as in FIG. 5C. FIG. 5E is a graphical representation of mean velocity (Vm) plotted against time; the eight data points shown are from the location of the most linear portion of the Vm change during the breath-holding maneuver, when the subject is at a 30 degree-HUT. FIG. 5F is a graphical representation of the regression line from Vm plotted against cardiac cycle; the circles are the same as in FIG. 5E. FIG. 5G is a graphical representation of mean velocity (Vm) plotted against time; the eight data points shown are from the location of the most linear portion of the Vm change during the breath-holding maneuver, when the subject is at a 45 degree-HUT. FIG. 5H is a graphical representation of the regression line from Vm plotted against cardiac cycle; the circles are the same as in FIG. 5G.

When Vm was plotted against cardiac cycle, the linearity of the slope became more recognizable graphically (FIGS. 5B, 5D, 5F, and 5H). Many studies have shown that when end-tidal P$_{CO2}$ (PET$_{O2}$) exceeds a certain threshold (break point), the CBFV increases linearly with time and this break point is different from subject to subject. Here, finding this break point was essentially achieved by calculating the most linear portion of Vm during a breath-holding maneuver (FIGS. 5A, 5C, 5E, and 5G).

Previous studies have required capturing each data point separately, one for each value of PET$_{CO2}$ desired. Those experiments required a gas analyzer and a complex rebreathing apparatus; several data points were captured individually by resetting the PET$_{CO2}$ value and recording the average CBFV. Many iterations of rebreathing experiments were needed to form a curve on which regression could be done; thus, there is an inherent fundamental limit on temporal sampling. This limit is caused by the need to average CBFV which is measured every cardiac cycle (72 beats/min), to match the change in (PET$_{CO2}$) which is measured every breath (12 breaths/min). Averaging CBFV values hinders the ability to detect the fast-hemodynamic change during hypercapnia. Another limitation of prior methods is the complexity of using additional equipment.

In contrast, the methods disclosed here has high temporal resolution both during the breath-hold maneuver (100 samples/second) and in the regression curve (one sample per cardiac cycle). Temporal resolution and the ability to measure CBVF every cardiac cycle is one of the major advantages of TCD in comparison with fMRI. Moreover, BHAI does not introduce undue technical difficulty as it is essentially a linear regression on a select portion of the CBFV response curve. This method has the advantages of simplicity, portability, and the ability to harness the high temporal resolution of TCD to evaluate CVR. These advantages make BHAI an ideal biomarker for several neurodeficits affecting CVR, such as preclinical Alzheimer's screening in hospitals and the senior living community. Diagnosing preclinical Alzheimer's disease leads to a better chance of delaying or preventing the onset of Alzheimer's disease, especially if management or therapeutic interventions are initiated before the synaptic loss and neuronal death occur in an embodiment, MAI can be combined with one or more of other biomarkers to screen for patients with preclinical Alzheimer's disease and to predict the development of Alzheimer's disease dementia. Other such biomarkers include biomarkers in cerebrospinal fluid (Aβ$_{42}$, tau, and phosphor-tau), non-invasive neuroimaging, and genetic evidence of Alzheimer's disease. Further neuro-imaging techniques, such as Functional MM, diffusion tensor imaging MRI, arterial spin labeling (ASL) MRI, and advanced PET imaging, can be used to characterize the disease in patients who present abnormal BHAI and provide appropriate therapeutic and disease management regimens.

Figure 6:
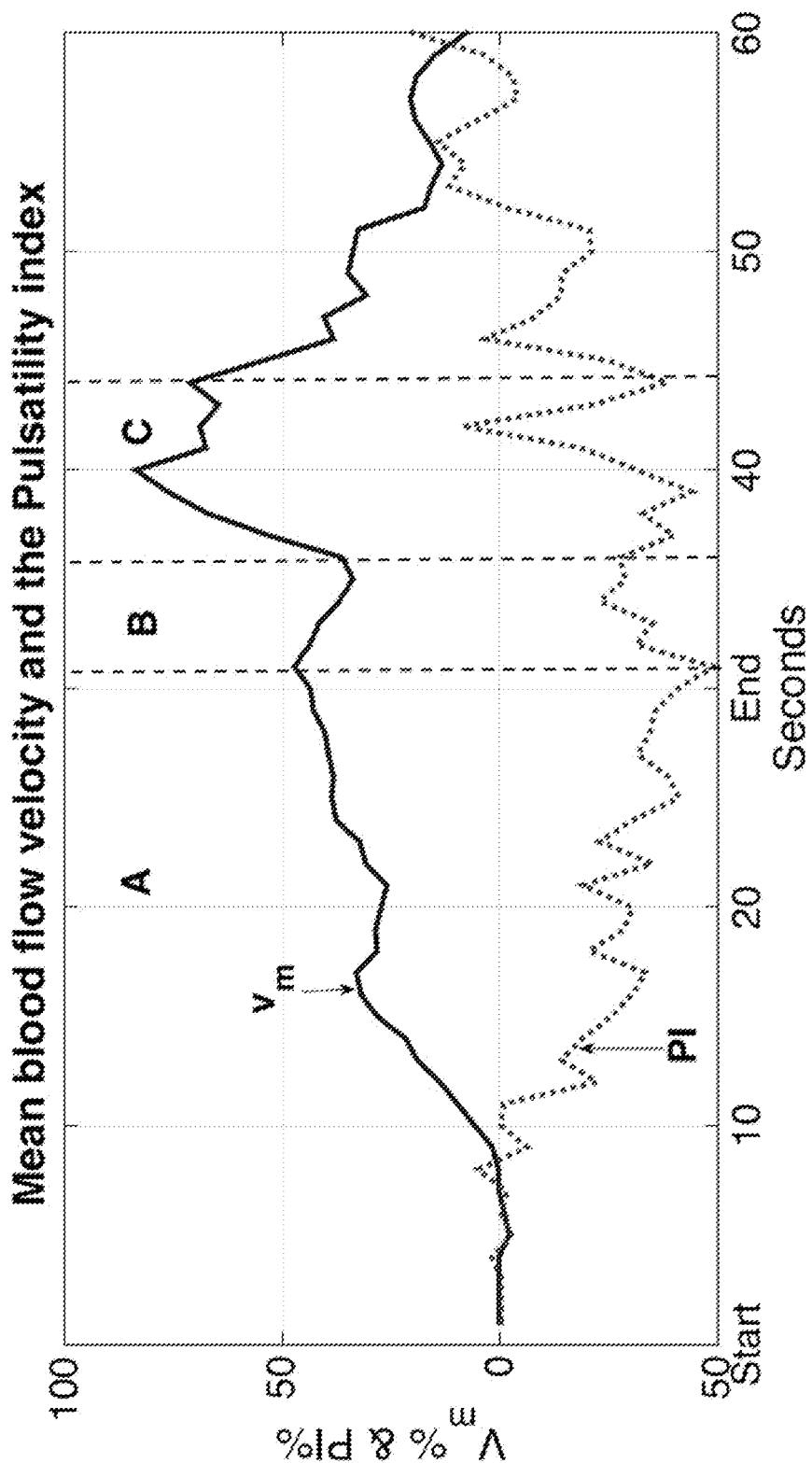
FIG. 6 is a graphical representation of the blood flow velocity in the middle cerebral artery (continuous line) and the pulsatility index (dotted line) for one subject during the BH maneuver (the value is normalized to baseline to observe the trend). Start on the X-axis is the starting time of the breath-holding maneuver, and End is the end time of the breath-holding maneuver. Vm=mean blood flow velocity; PI=pulsatility index.

Additionally, the data suggested that CVR does not change with body position, although cerebral perfusion pressure may be higher in HDT. Observed power (post hoc power analysis) was conducted to show that even with 10 subjects a sufficiently high probability existed of finding true effects using BHAI (FIG. 6). In other words; the improved sensitivity of an index such as BHAI (in contrast to BHI) was needed to confirm lack of a CVR/body position relationship. This finding is consistent with recent studies showing the subject position, HUT or supine or HDT, does not alter the CVR. This finding indicates that intracranial blood flow is well maintained by the CA process during significant changes in body position. Additionally, the result that CVR values were not increasing with HDT would suggest that CA is not responsible for regulating CVR. The dilatory effects on the cerebral arterioles and capillaries caused by CVR have a different mechanism compared with CA. This may explain the reason that CVR is impaired in subjects with Alzheimer's disease, but CA is preserved.

One of the biggest limitations of using TCD to evaluate CVR is the change in middle cerebral artery diameter during severe alterations in CO$_2$. Recent MM studies have shown both dilation of the middle cerebral artery during hypercapnia and constriction of the middle cerebral artery during hypocapnia. This causes CBFV to underestimate CBF during hypercapnia and overestimate CBF during hypocapnia. In the methods disclosed here, PI was always inversely related to CBFV during the breath-holding maneuver (Section A of FIG. 6) and shortly after the breath-holding maneuver (Section B of FIG. 6). Surprisingly, CBFV had a spike in all subjects after about 2-4 seconds of the end of breath-holding maneuver, and interestingly, this was the only part of the CBFV curve where PI was positively correlated to CBFV (Section C of FIG. 6). Examining the relationship between PI and Vm might help overcome this limitation without using any additional imaging modalities. This unexpected spike of CBFV may be caused by overestimating CBFV during hypocapnia. It may be that hypocapnia is induced by the involuntary deep breath to overcome the excessive amount of CO$_2$ triggered by the breath-holding maneuver. If the change in CBFV is negatively correlated (out of phase) with the PI, the assumption of a fixed middle cerebral artery is valid (Sections A and B of FIG. 6). However, if the change in CBFV is positively (in phase)

correlated to the PI, the assumption of a fixed middle cerebral artery is not valid (FIG. 6). In some previous studies, BHI values may have been overestimated due to the inclusion of this spike as part of breath-holding maneuver.

BHAI was successful in the assessment of CVR using a breath-holding maneuver. BHAI has less variability when compared with the conventional standard BHI and is not computationally difficult. Additionally, CVR did not significantly change due to body position. This was unexpected considering cerebral perfusion pressure may be higher in HDT due to induced gravity-dependent shifts in blood volume distribution. Pulsatility index (PI) is inversely related to CBFV both during the breath-hold maneuver and shortly after the breath-hold maneuver. Interestingly, about 2-4 seconds after the breath-hold maneuver, a spike occurs in CBFV which is positively correlated to PI (Section B of FIG. 6).

Example 2

Study Subjects. All subjects were examined at a single site, the Department of Neurological Sciences (DONS) at the University of Nebraska Medical Center (UNMC). Subjects were enrolled between November 2016 and August 2018. All subjects were consented according to a protocol approved by both the University of Nebraska-Lincoln's (UNL) and UNMC Institutional Review Boards (IRB). For patients diagnosed with dementia, another written consent was obtained from patients' legally authorized representative (LAR). A total of 27 subjects participated in this study. The study population was divided into three groups: healthy subjects, patients diagnosed with mild to moderate Alzheimer's disease, and participants identified as preclinical Alzheimer's disease (Table 3). Healthy and preclinical subjects were recruited as part of an ongoing Anti-Amyloid Treatment in Asymptomatic Alzheimer's study (A4 Study; NCT02008357). As a result, healthy and preclinical subjects had biomarker evidence supporting their diagnosis before the study. Healthy and preclinical subjects were both cognitively normal as determined by a Mini-Mental State Examination (MMSE) score of 27-30, and Global Clinical Dementia Rating (CDR) scale score of 0. The distinction between healthy and preclinical subjects was made by biomarkers of brain amyloid beta (Aβ) amyloidosis, using increased amyloid tracer retention on positron emission tomography (PET) imaging. Alzheimer's disease subjects had clinical evidence of mild cognitive impairment consistent with prodromal Alzheimer's disease or mild dementia consistent with probable Alzheimer's disease dementia with evidence of the Alzheimer's disease pathophysiological process. All Alzheimer's disease subjects had evidence of elevated cortical amyloid deposition on an amyloid PET scan that was obtained as part of one of three clinical trials for subjects with prodromal to mild Alzheimer's disease (Expedition 3 trial NCT01900665; CREAD 2 trial NCT03114657; or IDEAS trial NCT02420756).

TABLE 3

Demographic features of control, Preclinical-Alzheimer's disease, and Alzheimer's disease participants

| Characteristics | Control N = 9 | Preclinical-AD N = 8 | AD N = 10 | P Value |
|---|---|---|---|---|
| Age (y) | 71.3 ± 3.8 | 75 ± 7.6 | 68.1 ± 5.1 | 0.03† |
| Gender (M:F) | 4:5 | 5:3 | 4:6 | 0.63 |
| Education (y) | 17.4 ± 2 | 16.2 ± 2.3 | 16.4 ± 3.8 | 0.65 |
| BMI | 32.4 ± 5.8 | 27.4 ± 5.4 | 24.2 ± 3.7 | 0.006* |
| Handedness (R:L) | 9:0 | 8:0 | 8:2 | 0.5 |

AD = Alzheimer's disease; TCD = transcranial doppler; M = male; F = female; Y = years; BMI = body mass index; R = right handed subjects; L = left handed subjects.
Values are presented as mean ± standard deviation (range)
*P < 0.05 for Tukey-Kramer's mulitple comparison (post hoc) test between health and AD.
†P < 0.05 for Tukey-Krames's mulitple comparison (post hoc) test between preclinical-AD and AD.

Beta-amyloid PET images were obtained using Florbetapir F18 Injection (Amyvid, Eli Lilly and Company, Philadelphia, PA). This radiopharmaceutical binds to beta-amyloid and is used to estimate neuritic plaque density. Subjects were given a maximum of 10 milliCurie (mC) dose of Amyvid, followed by a 10-minute PET image acquired starting 30 to 50 minutes after injection. For all of control and preclinical Alzheimer's disease subjects and all but one of the Alzheimer's disease subjects, images were uploaded and read by a neuroradiologist from a dedicated neuroimaging company (Molecular NeuroImaging, Boston, MA). The neuroradiologist performed a binary categorization (elevated vs. non-elevated) analysis of beta-amyloid burden. One Alzheimer's disease patient image was read visually by a local radiologist, and an elevated level of beta-amyloid was confirmed. All participants were carefully screened by a board-certified neurologist to identify the cause of dementia. All subjects had low cerebrovascular disease burden based upon a clinical exam that consisted of completion of the NIH Stroke Scale (NIHSS) and calculating a Revised Haschinski Ischemic Scale (HIS) score from the subject's history and exam. A HIS score of 1 or less does not suggest a vascular cause of cognitive impairment with high sensitivity and specificity in previous studies.

Neuropsychological Tests.

Neuropsychological tests and estimates of dependence level and dementia stage were determined for all participants. These tests and scales included the following:

Mini-Mental State Examination (MMSE) is a thirty-point questionnaire used widely to measure cognitive decline. The mean score for cognitively normal individuals is 27.6, and a single cutoff score of 24 indicates some abnormality.

Animal naming is a measure of verbal fluency and semantic memory, where participants name as many animals as possible in 60 seconds, and the final score is the number of distinct animals named. A score less than 14 suggests cognitive impairment.

Digit Symbol Substitution Test (DTST) is a measure of information processing speed and psychomotor speed. It is a pencil and paper test where participants are presented with letters and their corresponding symbols. Then participants are given random letters, and they need to fill in the matching symbols. The score is the number correct matching in 90 seconds and the range for cognitively normal old adults is 38.8-66.8.

The Dependence Scale (DS) measures the amount of assistance needed to perform daily activities. DS scores range from 0 to 15, where lower scores indicate mild dependence (e.g., the patient needs frequent help finding misplaced objects), and high scores indicate severe reliance (e.g., the patient cannot feed themselves).

The Clinical Dementia Rating (CDR) is a five-point scale measure of dementia severity in each of six cognitive and functional domains (Memory, Orientation, Judgment and Problem Solving, Community Affairs, Home and Hobbies, and Personal Care). The global CDR score is calculated using a specific scoring algorithm in which normal=0, very mild dementia=0.5, mild dementia=1, moderate dementia=2, and severe dementia=3. The Clinical Dementia Rating Scale Sum of Boxes Scores (CDR-SOB) is identical to CDR, but the final score is calculated by merely summing each of the domain box scores, unlike CDR which requires an algorithm for computation. CDR-SOB scores range from 0 to 18, and higher scores correlate to severity of dementia.

The Revised Hachinski Ischemic Scale (HIS) is a modified test of the widely used HIS. HIS is a widely used method of identifying vascular dementia. Modified HIS is seven scales tests with binary scoring (0,1). A total of two or higher indicates a vascular component of cognitive impairment.

Protocol. Prior to TCD evaluation, participants underwent a physical exam including height, weight, heart rate, heart rhythm, blood pressure and completion of the NIH Stroke Scale by a physician. Cognitive tests, the Dependence Scale and the HIS were completed on the day of the TCD evaluation. The CDR was completed by a certified rater within 6 months of the TCD evaluation. TCD evaluation consisted of a basal ultrasound examination performed using a commercial transcranial Doppler machine (Doppler BoxX, Compumedics Germany Gmbh) by a trained examiner (MA) who was blinded to the cognitive diagnosis of the subjects. The participants were placed in the upright position, and TCD transducers were fixed on the temporal windows using a custom fixation device. For each subject, proximal segments of the middle cerebral artery were insonated at depths of 43-55 mm, with Doppler gate size between 8- and 10-mm. The transducer center frequency was 2 MHz. The depth was initially set to expected depths for the middle cerebral artery, and the strongest signal found by manual adjustment of the depth and transducer position. Once the signal was optimized, the transducer was locked in place. After middle cerebral artery identification and transducer fixation, subjects rested for a short period of three minutes to establish a CBFV baseline. Mean flow velocity (MFV), pulsatility index (PI), peak systolic velocity (Vs), and end diastolic velocity (Vd) were calculated during the bassline period. Then, subjects performed a breath-hold procedure. Subjects were instructed to breathe normally until told to begin breath holding following a normal inspiration. The subjects were instructed not to begin their breath hold by performing a Valsalva maneuver, but simply to stop breathing following inhalation and hold their breath as long as they could up to a maximum of 30 seconds. After the breath-hold procedure, the subjects again rested for at least two minutes. Finally, CVR was estimated using two methods. First, the BHI was obtained by calculating the percentage change from MFV during baseline and the maximal increase in flow velocity at the end of the breath-hold. This percentage change was divided by 30 seconds (or the actual time subjects held their breath). Second, BHAI and CVR was calculated by linear regression of the most linear portion of the MFV change during the breath-hold maneuver. During the experiment, end-tidal $CO_2$ ($ETCO_2$) was assessed using a nasal cannula and capnograph (Omni K Infinium USA) to ensure a proper breath-hold procedure, especially for subjects with dementia.

Data Processing.

Blood flow velocity data were recorded and then exported for further analysis in MATLAB (R2018a v. 9.4.0, Mathworks, Natick, MA, USA). A customized MATLAB program was written for all processing of TCD envelope waveforms obtained during the experiment. Data were analyzed in the same manner as previously reported. Briefly, the mean velocity MFV was calculated by averaging the CBFV samples within each cardiac cycle. Then, PI for each cardiac cycle was calculated by subtracting diastolic velocity (Vd) from the systolic velocity (Vs), and then dividing by the MFV[11]. Finally, CVR was calculated using both BHI and BHAI indices.

Statistical Analysis.

The experiment followed a completely randomized design with unequal sample sizes. Means and standard deviations were calculated for all quantitative variables. Frequencies and proportions were calculated for all categorical variables. The Lilliefors test was used to check the normality assumption of the data. Between-group differences of quantitative normally distributed variables were assessed using ANOVA, and non-parametric Kruskall-Wallis tests were used for categorical data and non-normally distributed quantitative variables. Post-hoc analysis with Tukey-Kramer adjustment were applied to compare between means. Correlations between BHAI and quantitative cognitive tests were evaluated using Pearson correlation (or Spearman's rank correlation if normality assumptions were violated). An alpha level of less than 0.05 was considered statistically significant. All statistics were computed using the MATLAB Statistics and Machine Learning Toolbox.

The demographic data of all subjects are summarized in Table 3. Although the ages of Alzheimer's disease subjects differed from preclinical subjects, the mean preclinical age was not significantly different from the control group. There were no statistical differences between groups in the distribution by gender or education. A significant difference was found in body mass index between control and Alzheimer's disease. The medical history of all subjects is summarized in Table 4. There were no significant differences in vascular risk, smoking, history of diabetes, treatment for hypertension, or diastolic blood pressure. However, systolic blood pressure was significantly lower in the Alzheimer's disease group.

TABLE 4

Medical History and Exam Findings of control, Preclinical-Alzheimer's disease, and Alzheimer's disease participants

| Characteristics | Control N = 9 | Preclinical-AD N = 8 | AD N = 10 | P Value |
|---|---|---|---|---|
| Systolic (mmHg) | 137.8 ± 13 | 132.75 ± 11.2 | 115.2 ± 15.3 | 0.003*,† |
| Diastolic (mmHg) | 80.8 ± 8.1 | 74.5 ± 12.3 | 71.6 ± 10.4 | 0.16 |
| Smoking | 0 (0%) | 1 (12.5%) | 0 (0%) | 0.3 |
| Diabetes | 2 (22%) | 1 (12.5%) | 0 (0%) | 0.54 |
| Treatment for hypertension | 5 (56%) | 3 (37.5%) | 1 (10%) | 0.089 |
| HIS | 0.11 ± 0.33 (0~1) | 0 ± 0 (0~0) | 0.2 ± 0.43 (0~1) | 0.42 |

AD = Alzheimer's disease; mmHg = millimeter of mercury; HIS = revised Hachinski Ischemic Scale.
Values are presented as mean ± standard deviation (range) or number (percentage).
*P <0.05 for Tukey-Kramer's multiple comparison (post hoc) test between healthy and Alzheimer's disease.
†P < 0.05 for Tukey-Kramer's multiple comparison (post hoc) test between preclinical-Alzheimer's disease and Alzheimer's disease.

All cognitive tests are significantly lower in Alzheimer's disease subjects (Table 5), which included MMSE, DS, CDR, CDR-sob, animal naming, and DSST.

TABLE 5

Cognitive tests dependence and dementia staging of control, Preclinical-Alzheimer's disease, and Alzheimer's disease participants.

| Characteristics | Control N = 9 | Preclinical-AD N = 8 | AD N = 10 | P Value |
|---|---|---|---|---|
| MMSE | 29.7 ± 0.7 (28~30) | 28.1 ± 0.8 (27~29) | 21.2 ± 5.9 (9~28) | <0.001*, † |
| Animal Naming | 22.1 ± 5.8 (16~32) | 18.5 ± 3.9 (14~23) | 10.5 ± 5.0 (2~17) | <0.001*, † |
| DSST | 47.3 ± 7.9 (35~56) | 44 ± 8.7 (39~65) | 11.4 ± 12.02 (1~38) | <0.001*, † |
| DS | 0 ± 0 (0~0) | 0.13 ± 0.35 (0~1) | 4.4 ± 1.5 (2~7) | <0.001*, † |
| CDR | 0 ± 0 (0~0) | 0 ± 0 (0~0) | 0.75 ± 0.3 (0.5~1) | <0.001*, † |
| CDR-SOB | 0 ± 0 (0~0) | 0.13 ± 0.23 (0~0.5) | 4.2 ± 1.0 (3~6) | <0.001*, † |

AD = Alzheimer's disease; MMSE = Mini-mental state examination; DS = dependence scale; CDR = clinical dementia rating; CDR-SOB = clinical dementia rating scale sum of boxes; DSST = digit symbol substitution test.
Values are presented as mean ± standard deviation (range)
*P < 0.05 for Tukey-Kramer's mulitple comparison (post hoc) test between healthly and Alzheimer's disease.
†P < 0.05 for Tukey-Kramer's mulitple comparison (post hoc) test between preclinical-Alzheimer's disease and Alzheimer's disease.

TCD parameters are summarized in Table 6.

TABLE 6

TCD parameters of control, Preclinical-Alzheimer's disease and Alzheimer's disease participants

| TCD variables | Control N = 9 | Preclinical-AD N = 8 | AD N = 10 | P Value |
|---|---|---|---|---|
| MFV (cm/s) | 54.6 ± 12.1 | 53.4 ± 6.7 | 49 ± 8.6 | 0.41 |
| Vs (cm/s) | 86.7 ± 19.42 | 84.29 ± 9.44 | 86.3 ± 11.56 | 0.9 |
| Vd (cm/s) | 21.6 ± 7.67 | 22.5 ± 6.53 | 8.9 ± 5.61 | <0.001*, † |
| PI | 1.2 ± 0.2 | 1.16 ± 0.13 | 1.64 ± 0.18 | <0.001*, † |
| BM | 1.23 ± 0.22 | 1.19 ± 0.18 | 0.882 ± 0.23 | 0.0025*, † |
| BHAI | 1.07 ± 0.11 | 0.71 ± 0.28 | 0.51 ± 0.17 | <0.001*, ‡ |

IVIFV = mean flow velocity; Vs = systolic velocity; Vd = diastolic velocity; PI = pulsatility index. BHI = breath holding index; BHAI = breath-hold acceleration index.
Values are presented as mean ± standard deviation
*P < 0.05 for Tukey-Kramer's multiple comparison (post hoc) test between control and Alzheimer's disease.
†P < 0.05 for Tukey-Kramer's multiple comparison (post hoc) test between preclinical-Alzheimer's disease and Alzheimer's disease.
‡P < 0.05 for Tukey-Kramer's multiple comparison (post hoc) test between healthy and preclinical Alzheimer's disease.

There were no significant differences in MFV and systolic velocity (Vs). PI was significantly increased, and diastolic velocity significantly decreased, in Alzheimer's disease patients in comparison with preclinical and control participants. An opposite pattern was found for BHI, where Alzheimer's disease patients had significantly lower values in comparison with control and preclinical. Finally, BHAI was significantly higher in control subjects in comparison with preclinical participants and Alzheimer's disease patients. BHAI was able to distinguish between healthy and preclinical subjects with high statistical significance (FIGS. 7A and 7B).

Figures 7A, 7B:
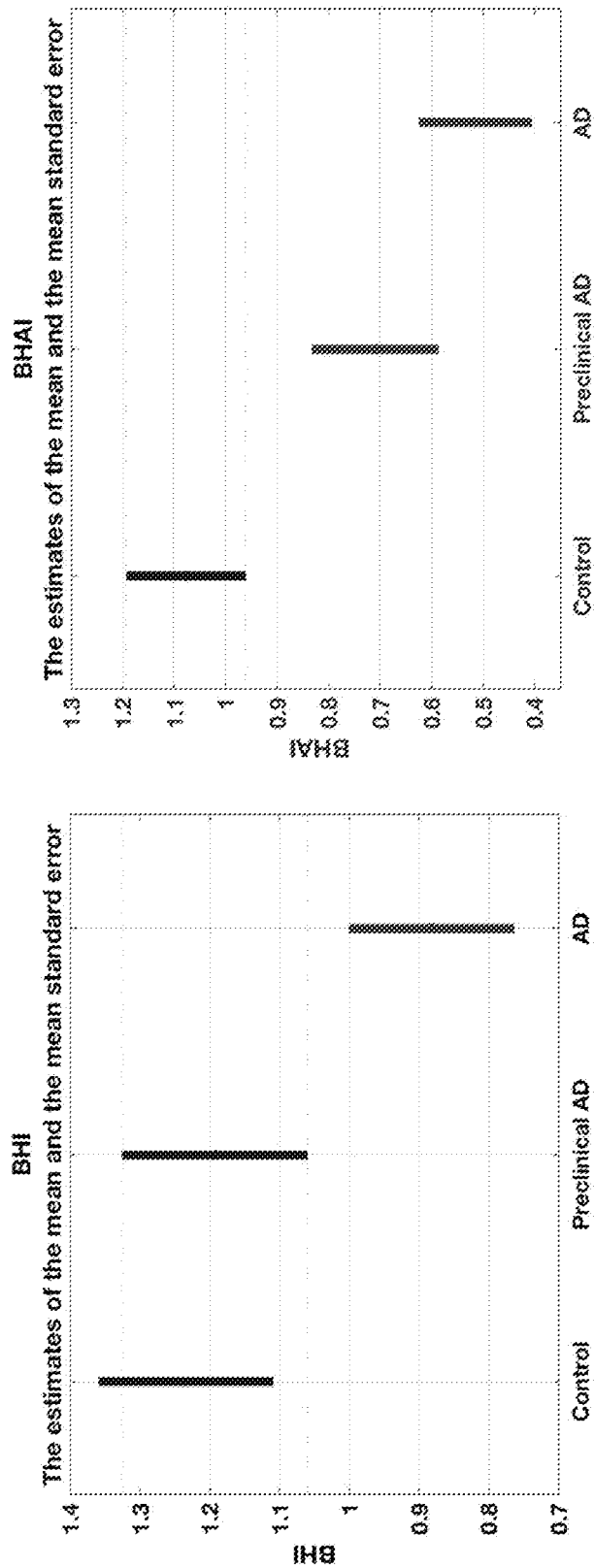
FIGS. 7A and 7B are graphical representations of the results of BHAI and BHI evaluation, respectively, on healthy subjects, patients with preclinical Alzheimer's disease, and patients with Alzheimer's disease. Multiple comparisons were made using Tukey adjustment; different colors indicate statistical significance (p<0.05). Note the BHI index (FIG. 7A) was able to differentiate only between asymptomatic and symptomatic participants. BHAI (FIG. 7B) was able to significantly differentiate not only between healthy subjects and patients with Alzheimer's disease, but also between healthy subjects and participants who have asymptomatic preclinical Alzheimer's disease.

FIGS. 7A and 7B are graphical representations of the results of BHAI and BHI evaluation, respectively, on healthy subjects, patients with preclinical Alzheimer's disease, and patients with Alzheimer's disease. Multiple comparisons were made using Tukey adjustment; different colors indicate statistical significance (p<0.05). BHAI was significantly correlated with MMSE (Pearson correlation coefficient (r)=0.73, P<0.01), CDR-SOB (r=−0.65, P<=0.001), animal naming (r=0.4414, P=0.02) and DSST (Spearman's rho coefficient (rs)=0.54, P=0.0034). Note the BHI index (FIG. 7A) was able to differentiate only between asymptomatic and symptomatic participants. BHAI (FIG. 7B) was able to significantly differentiate not only between healthy subjects and patients with Alzheimer's disease, but also between healthy subjects and participants who have asymptomatic preclinical Alzheimer's disease.

BHI and BHAI were evaluated in their ability to estimate CVR. Preclinical and Alzheimer's disease subjects were distinguished by the BHAI measurement but not the BHI measurement. Alzheimer's disease and healthy subjects were distinguishable by both BHAI and BHI. This result demonstrated the ability of BHAI to predict subjects in the preclinical stage of Alzheimer's disease. BHAI is a sensitive measurement of CVR, which is one of the three regulatory mechanisms on cerebral blood flow (the other two being autoregulation and the autonomic nervous system). Brain perfusion is very sensitive to changes in arterial carbon dioxide concentration.

CVR measures the ability of the cerebral arterioles to vasodilate in response to arterial carbon dioxide, and impaired CVR indicates the inability of cerebral arterioles to fully vasodilate under hypocapnic conditions. BHAI was able to detect the impairment in the vasodilation response because unlike BHI which uses only two time points to estimate CVR, BHAI was developed based on a regression along eight consecutive time points, and is thus a more robust measure. Additionally, the BHI formula assumes a linear relationship between cerebral blood (CBF) flow and $CO_2$. Methods based on BHAI were developed to account for the sigmoidal curve relationship between CBF and $CO_2$, approaching a plateau at the end of the breath holding procedure.

Moreover, PI was significantly higher in Alzheimer's disease patients than preclinical and healthy participants. This finding is consistent with recent studies showing higher PI and lower BHI in Alzheimer's disease subjects. PI measures downstream cerebral vascular resistance. It has been suggested that increased PI indicates insufficient blood flow to the brain. However, in the experiments here, the MBV did not show differences between healthy and Alzheimer's disease patients. The insignificant mean differences in MBV and the significant mean differences in PI can be explained by examining peak systolic velocity (Vs) and end diastolic velocity (Vd). From the data it can be seen that the reason for the rise in PI is a sharp decrease in Vd. It is interesting that decreased Vd also results from increased intracranial pressure and traumatic brain injury. Many previous TCD studies that examined cerebral blood flow in Alzheimer's disease subjects reported MFV and PI, which can be derived from the flow velocity envelope. However, most do not report Vs and Vd which are obtained from the velocity envelope signal. Examination of all indices might provide more perceptiveness to understand the complicity of the overlapping regulatory mechanism of cerebral blood flow.

Epidemiological studies show that stroke risk factors such as diabetes, smoking, hypertension and history of stroke are associated with Alzheimer's disease. The HIS results showed no significant stroke risk factors between groups. Thus, TCD parameters were independent of stroke risk factors. Furthermore, population-based studies showed that obesity significantly increases the risk for Alzheimer's disease. However, patients with Alzheimer's disease, regardless of severity, have lower BMI than cognitively intact patients, consistent with the results here. Alzheimer's disease patients had a significantly lower BMI compared with cognitively normal participants. Although Alzheimer's disease subjects were slightly younger than control and preclinical, no changes in CVR with age were observed in a population study in subjects above 50 years old. Another finding of this study was the moderate correlation between BHAI and MMSE. This correlation between CVR and MMSE was consistent with previous published research.

It should be understood that although the technology herein has been specifically disclosed by certain aspects, embodiments, and optional features, modification, improvement and variation of such aspects, embodiments, and optional features can be resorted to by those skilled in the art, and that such modifications, improvements and variations are considered to be within the scope of the following claims.

What is claimed is:

1. A method of detecting compromised cerebrovascular reactivity in a subject, comprising the steps of:
    acquiring a set of transcranial Doppler signals from a subject during performance of a breath-hold maneuver by the subject and calculating cerebral blood flow velocity (CBFV) measurements in response to the set of transcranial Doppler signals;
    acquiring a set of cardiac measurements of the subject during performance of the breath-hold maneuver, wherein the set of cardiac measurements include systolic velocity (Vs) and diastolic velocity (Vd) in each cardiac cycle for cardiac cycles during the breath-hold maneuver;
    calculating, using a processor executing computer-readable instructions, a mean velocity by averaging the CBFV measurements within each cardiac cycle;
    calculating, using the processor executing computer-readable instructions, a breath-hold acceleration index of the subject based on a linear regression correlation of temporal variations of the mean velocity across all cardiac cycles during the breath-hold maneuver;
    detecting presence of compromised cerebrovascular reactivity in the subject in response to the breath-hold acceleration index of the subject being more than one standard deviation less than a breath-hold acceleration index of a healthy individual performing the breath-hold maneuver under similar conditions as the subject; and
    administering a therapeutically effective compound or providing a behavioral modification regimen to the subject in response to detecting compromised cerebrovascular reactivity in the subject.

2. The method of claim 1, wherein the compromised cerebrovascular reactivity is indicative of asymptomatic, preclinical Alzheimer's disease.

3. The method of claim 1, wherein the compromised cerebrovascular reactivity is indicative of Alzheimer's disease in response to the breath-hold acceleration index of the subject being more than two standard deviations less than the breath-hold acceleration index of the healthy individual performing the breath-hold maneuver under similar conditions as the subject.

4. The method of claim 1, wherein the method further comprises the steps of:
    calculating, using the processor executing computer-readable instructions, a pulsatility index for each cardiac cycle during the breath-hold maneuver, wherein the pulsatility index is a quotient when the difference in the systolic velocity (Vs) and the diastolic velocity (Vd) in each cardiac cycle is divided by the mean velocity; and
    detecting presence of compromised cerebrovascular reactivity in the subject in response to an increased pulsatility index and the breath-hold acceleration index of the subject being more than one standard deviation less than the breath-hold acceleration index of the healthy individual performing the breath-hold maneuver under similar conditions as the subject.

5. The method of claim 4, wherein the compromised cerebrovascular reactivity is indicative of Alzheimer's disease.

6. The method of claim 1, wherein the transcranial Doppler signals are acquired in response to insonation of a basal cerebral artery.

7. The method of claim 1 further comprising the step of:
    fixing a transcranial Doppler transducer on a temporal window of a skull of the subject using a fixation device.

8. The method of claim 7, further comprising the steps of:
    adjusting a target depth of the transcranial Doppler transducer to an estimated expected depth for a middle cerebral artery of the subject, and
    determining an optimal strong signal by adjustment of depth and transducer position of the transcranial Doppler transducer.

9. The method of claim 1, wherein the breath-hold maneuver is performed by the subject for a predetermined breath-hold (BH) time or until the subject needs to exhale.

10. The method of claim 1, wherein the cardiac measurements are heartbeats.

11. The method of claim 1, wherein the linear regression correlation represents acceleration as a change in blood flow velocity per unit of time sampled at each cardiac cycle.

12. A method of treatment of preclinical Alzheimer's disease in a subject, comprising the steps of:
    acquiring a set of transcranial Doppler signals from a subject during performance of a breath-hold maneuver by the subject and calculating cerebral blood flow velocity (CBFV) measurements in response to the set of transcranial Doppler signals;
    acquiring a set of cardiac measurements of the subject during performance of the breath-hold maneuver, wherein the set of cardiac measurements include systolic velocity (Vs) and diastolic velocity (Vd) in each cardiac cycle for cardiac cycles during the breath-hold maneuver;
    calculating, using a processor, a mean velocity by averaging the CBFV measurements within each cardiac cycle;
    calculating, using the processor, a breath-hold acceleration index of the subject based on a linear regression correlation of temporal variations of the mean velocity across all cardiac cycles during the breath-hold maneuver;
    detecting presence of preclinical Alzheimer's disease in the subject in response to the breath-hold acceleration index of the subject being more than one standard deviation less than a breath-hold acceleration index of a healthy individual performing the breath-hold maneuver under similar conditions as the subject; and
    administering a therapeutically effective compound to the subject detected of having preclinical Alzheimer's disease.

13. The method of claim 12, wherein the therapeutically effective compound is an anti-amyloid agent.

14. The method of claim 12, wherein the therapeutically effective compound is solanezumab or verubecestat or aducanumab.

15. The method of claim 12, wherein the transcranial Doppler signals are acquired in response to insonation of a basal cerebral artery.

16. The method of claim 12, further comprising the step of:
fixing a transcranial Doppler transducer on a temporal window of the subject using a fixation device;
adjusting a target depth of the transcranial Doppler transducer to an estimated expected depth for a middle cerebral artery of the subject; and
determining an optimal strong signal by adjustment of depth and transducer position of the transcranial Doppler transducer.

17. The method of claim 12, wherein the breath-hold maneuver is performed by the subject for a predetermined breath-hold (BH) time or until the subject needs to exhale.

18. A method of treating compromised cerebrovascular reactivity in a subject, comprising the steps of:
acquiring a set of transcranial Doppler signals from a subject during performance of a breath-hold maneuver by the subject and calculating cerebral blood flow velocity (CBFV) measurements in response to the set of transcranial Doppler signals;
acquiring a set of cardiac measurements of the subject during performance of the breath-hold maneuver, wherein the set of cardiac measurements include systolic velocity (Vs) and diastolic velocity (Vd) in each cardiac cycle for cardiac cycles during the breath-hold maneuver;
calculating, using a processor, a mean velocity by averaging the CBFV measurements within each cardiac cycle;
calculating, using the processor, a breath-hold acceleration index of the subject based on a linear regression correlation of temporal variations of the mean velocity across all cardiac cycles during the breath-hold maneuver;
detecting presence of compromised cerebrovascular reactivity in the subject in response to the breath-hold acceleration index of the subject being more than one standard deviation less than a breath-hold acceleration index of a healthy individual performing the breath-hold maneuver under similar conditions as the subject; and
administering a therapeutically effective compound to the subject, along with providing a behavioral modification regimen, in response to detecting compromised cerebrovascular reactivity in the subject.

19. The method of claim 18, wherein the therapeutically effective compound is one or more of an acetylcholinesterase inhibitor, a glutamate modulator, and an anti-amyloid agent.

20. The method of claim 18, wherein the behavioral modification regimen is one or more of exercise, psychotherapy, cognitive retraining, and skills training to regain cognitive functions.

* * * * *